United States Patent
Shimizu

(10) Patent No.: US 10,207,977 B2
(45) Date of Patent: Feb. 19, 2019

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi (JP)

(*) Notice: Subject to any disclaimer, the term of this patent is extended or adjusted under 35 U.S.C. 154(b) by 0 days.

(21) Appl. No.: 15/540,189

(22) PCT Filed: May 25, 2017

(86) PCT No.: PCT/JP2017/019575
§ 371 (c)(1),
(2) Date: Jun. 27, 2017

(87) PCT Pub. No.: WO2018/135016
PCT Pub. Date: Jul. 26, 2018

(65) Prior Publication Data
US 2018/0201563 A1    Jul. 19, 2018

(30) Foreign Application Priority Data

Jan. 18, 2017 (JP) ................................. 2017-006647
Mar. 2, 2017 (JP) ................................. 2017-039391

(51) Int. Cl.
| | |
|---|---|
| *C07C 51/12* | (2006.01) |
| *C07C 51/44* | (2006.01) |
| *B01D 3/00* | (2006.01) |
| *B01D 3/14* | (2006.01) |
| *B01D 15/36* | (2006.01) |

(52) U.S. Cl.
CPC .............. *C07C 51/12* (2013.01); *B01D 3/009* (2013.01); *B01D 3/143* (2013.01); *B01D 15/361* (2013.01); *C07C 51/445* (2013.01)

(58) Field of Classification Search
None
See application file for complete search history.

(56) References Cited

U.S. PATENT DOCUMENTS

| | | | |
|---|---|---|---|
| 9,458,077 | B2 | 10/2016 | Shaver et al. |
| 2007/0093676 | A1 | 4/2007 | Kojima et al. |
| 2008/0293966 | A1 | 11/2008 | Scates et al. |
| 2008/0293967 | A1 | 11/2008 | Scates et al. |
| 2015/0299084 | A1 | 10/2015 | Shimizu et al. |
| 2015/0368176 | A1 | 12/2015 | Miura et al. |
| 2016/0137574 | A1 | 5/2016 | Shaver et al. |

FOREIGN PATENT DOCUMENTS

| | | |
|---|---|---|
| EP | 1832569 A1 | 9/2007 |
| EP | 2937329 A1 | 10/2015 |
| EP | 29496407 A1 | 12/2015 |
| JP | 2006-182691 A | 7/2006 |
| JP | 2014-520107 A | 8/2014 |
| JP | 2016-121126 A | 7/2016 |
| WO | WO 2012/168396 A1 | 12/2012 |
| WO | WO 2012/168905 A1 | 12/2012 |
| WO | WO 2014/097867 A1 | 6/2014 |
| WO | WO 2014/115826 A1 | 7/2014 |
| WO | WO 2016/194850 A1 | 12/2016 |
| WO | WO 2017/057085 A1 | 4/2017 |

OTHER PUBLICATIONS

Corrected PCT International Search Report dated Sep. 12, 2017, in PCT International Application No. PCT/JP2017/019575.
Written Opinion of the International Searching Authority and International Search Report (forms PCT/ISA/237 and PCT/ISA/210), dated Aug. 1, 2017, for International Application No. PCT/JP2017/019575.
English translation of the Written Opinion dated Nov. 15, 2017, in PCT International Application No. PCT/JP2017/019575.
Extended European Search Report dated Mar. 12, 2018, in European Patent Application No. 17732015.7.
Japanese Office Action for Japanese Application No. 2017-533364, dated Apr. 17, 2018, with English translation.

*Primary Examiner* — Ana Z Muresan
(74) *Attorney, Agent, or Firm* — Birch, Stewart, Kolasch & Birch, LLP

(57) ABSTRACT

It is intended to provide a method capable of lowering a formic acid concentration in product acetic acid by a simple approach. The method for producing acetic acid according to the present invention comprises at least one step selected from a step that satisfies the following operating conditions (i) and a step that satisfies the following operating conditions (ii) in an acetic acid production process: (i) operating conditions involving a hydrogen partial pressure of less than 500 kPa (absolute pressure), a carbon dioxide partial pressure of less than 70 kPa (absolute pressure), and an operating temperature of more than 175° C.; and (ii) operating conditions involving a hydrogen partial pressure of not more than 5 kPa (absolute pressure), a carbon dioxide partial pressure of less than 20 kPa (absolute pressure), and an operating temperature of more than 100° C.

19 Claims, 5 Drawing Sheets

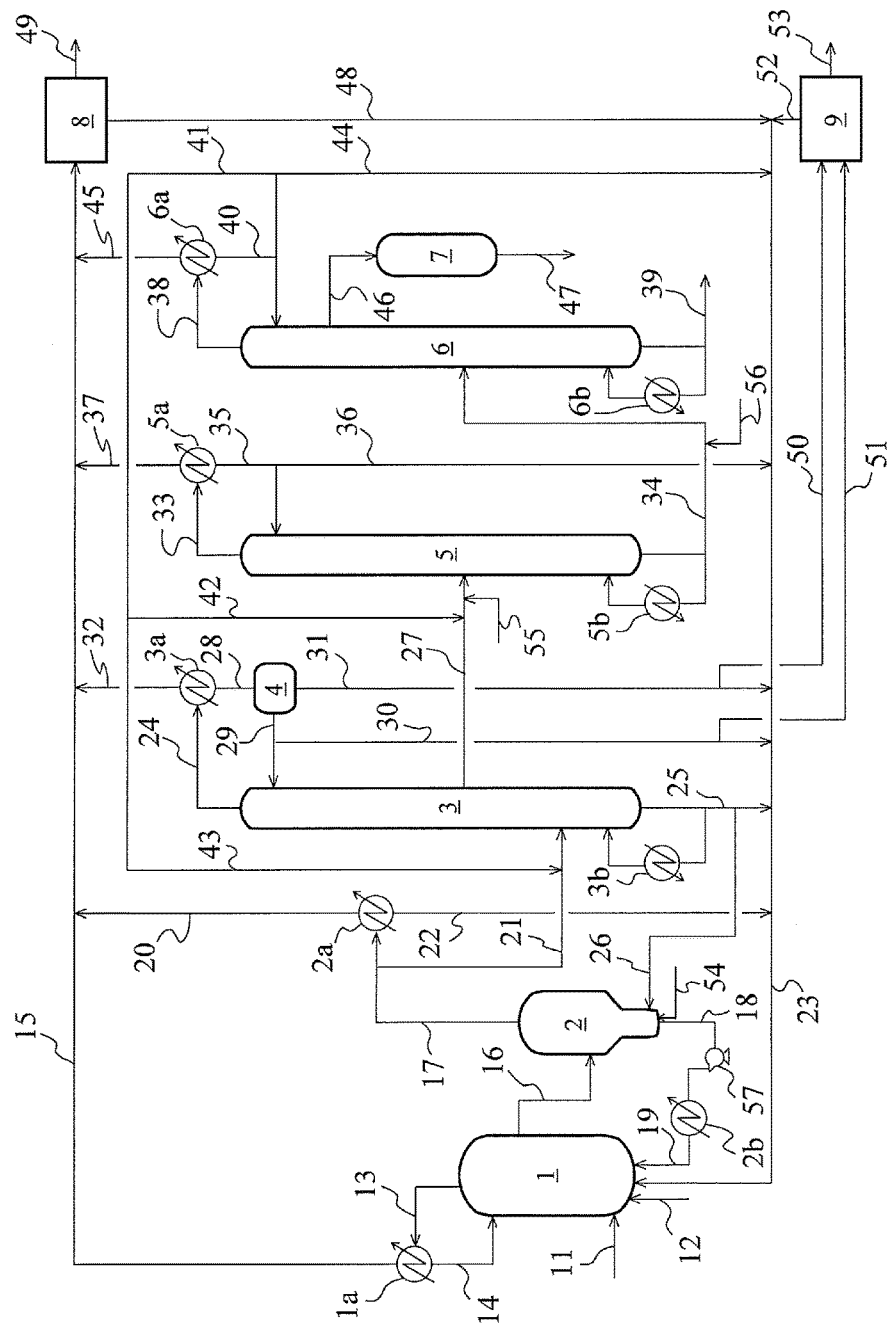
[Figure 1]

[Figure 2]
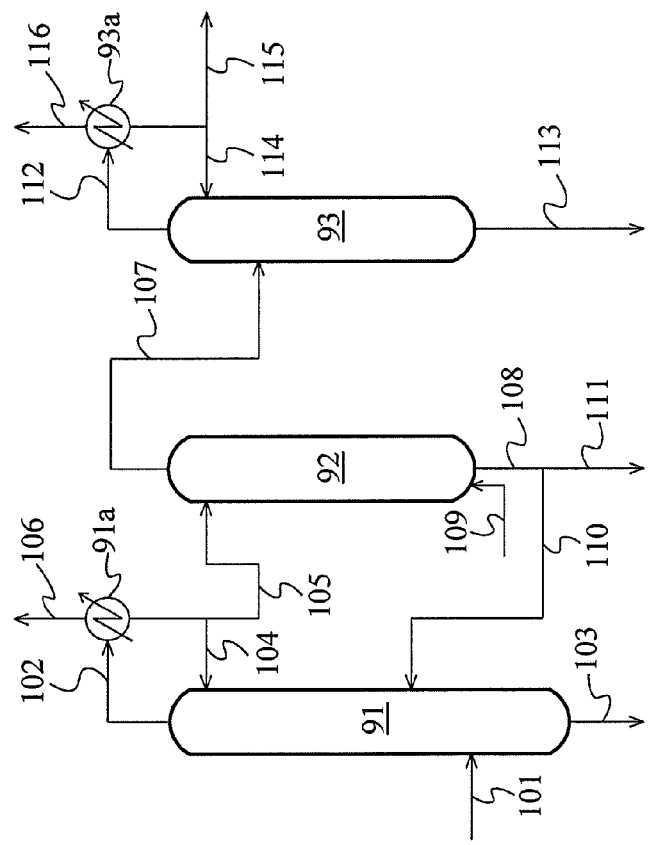

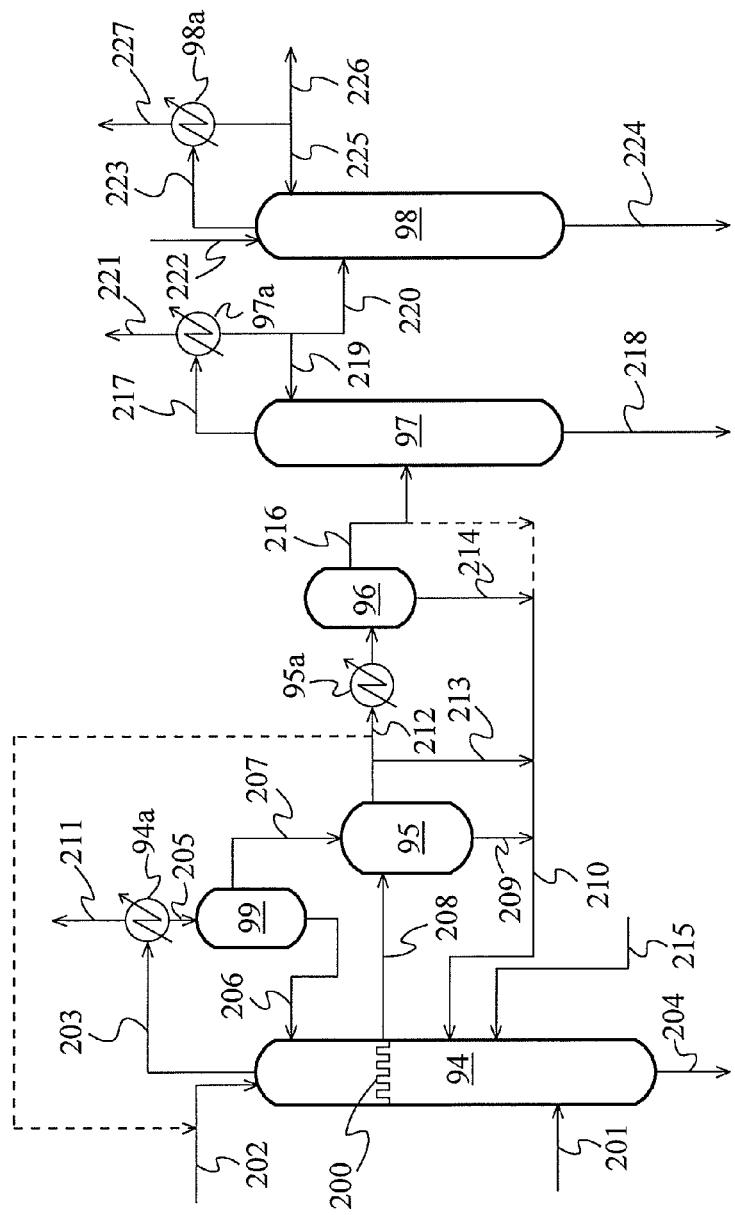
[Figure 3]

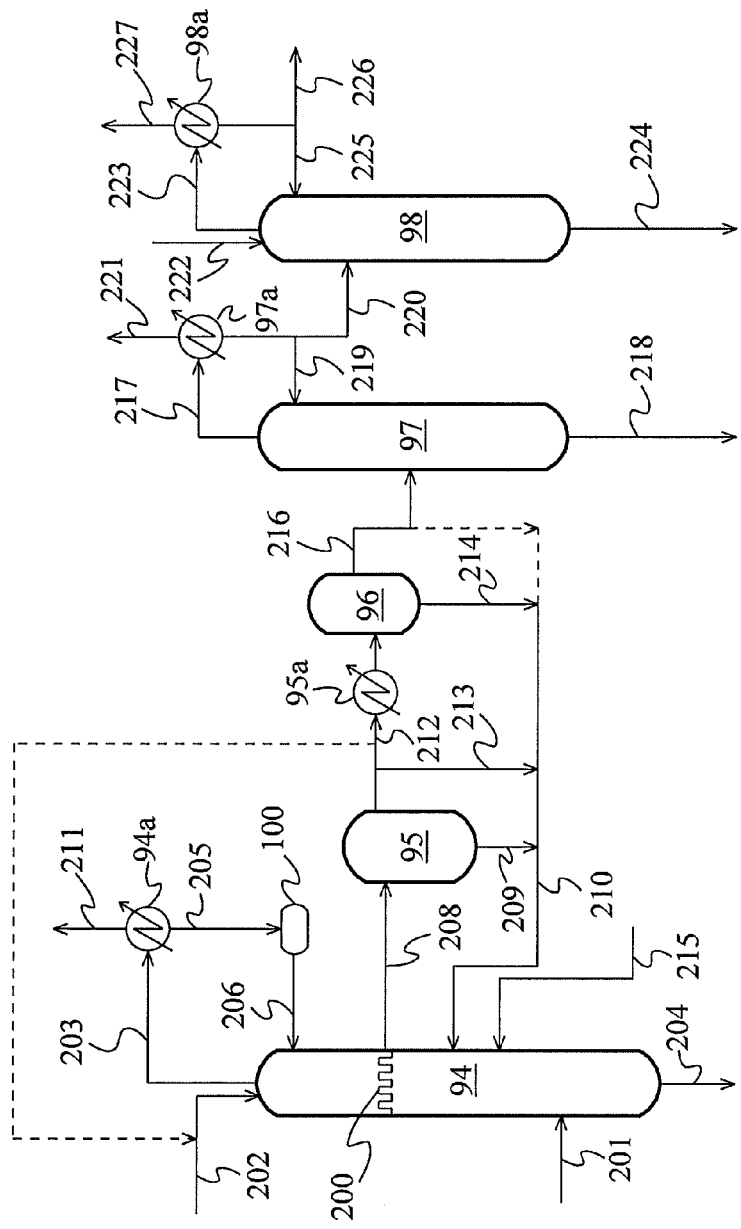
[Figure 4]

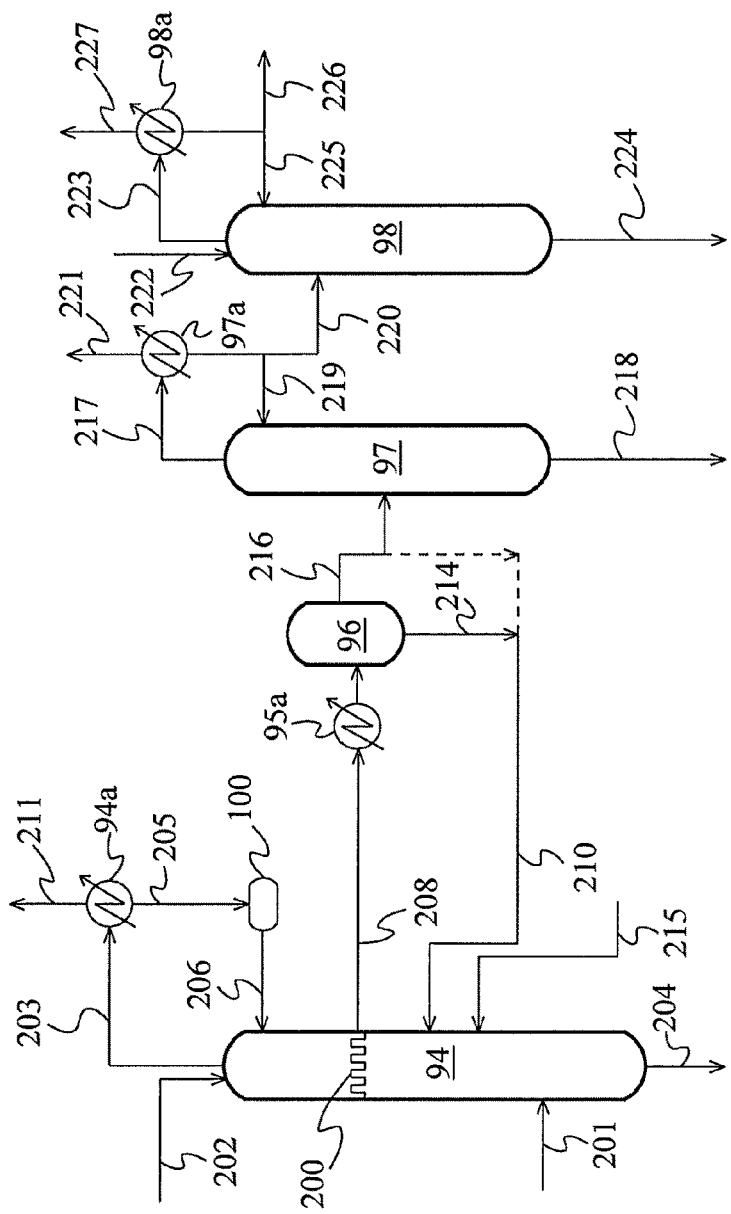
[Figure 5]

METHOD FOR PRODUCING ACETIC ACID

TECHNICAL FIELD

The present invention relates to a method for producing acetic acid. The present application claims the priorities of Japanese Patent Application No. 2017-006647 filed in Japan on Jan. 18, 2017 and Japanese Patent Application No. 2017-039391 filed in Japan on Mar. 2, 2017, the contents of which are incorporated herein by reference in their entirety.

BACKGROUND ART

A carbonylation process of a methanol method is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such an acetic acid production process, formic acid is produced as a by-product in the reaction vessel. The minimum amount of formic acid is favorable because the formic acid reduces the purity of product acetic acid. Patent Literatures 1 and 2 disclose that: formic acid is formed through the reaction of carbon monoxide with water; and therefore, the formic acid concentration in product acetic acid can be lowered by controlling a water concentration in a reaction medium to a low level. However, there is the problem that a catalyst becomes unstable if the water concentration in the reaction medium is decreased.

CITATION LIST

Patent Literature

Patent Literature 1: U.S. Patent Application Publication No. 2008/0293966
Patent Literature 2: U.S. Patent Application Publication No. 2008/0293967

SUMMARY OF INVENTION

Technical Problem

An object of the present invention is to provide a method capable of lowering a formic acid concentration in product acetic acid by a simple approach.

Solution to Problem

In order to attain the object, the present inventors have conducted diligent studies to discover a mechanism underlying formic acid formation and consequently gained the findings that: more than a little formic acid is formed, mainly, in a reaction vessel, an evaporator, and a lower boiling point component removal column where hydrogen and carbon dioxide are present; at a higher hydrogen partial pressure and carbon dioxide partial pressure, more formic acid is formed; at a higher temperature, formic acid formation is suppressed; the presence of equilibrium reaction of $H_2 + CO_2H \leftrightarrow HCOOH$ is predicted from these; etc. Accordingly, the present inventors have conducted further studies and found that: for suppressing formic acid formation, it is desirable to maintain a low hydrogen partial pressure, a low carbon dioxide partial pressure, and a high temperature; formic acid can be decomposed by recycling a process solution containing the formic acid to a reaction vessel, an evaporator, or a distillation column and maintaining a low hydrogen partial pressure, a low carbon dioxide partial pressure, and a high temperature; because formic acid has a lower boiling point than that of acetic acid and is therefore concentrated at the column top of each distillation column, a column top fraction of the distillation column is recycled to the reaction system or a distillation column positioned upstream from the distillation column so that formic acid can be decomposed; etc. The present invention is based on these findings and has been completed through further studies.

Specifically, the present invention provides a method for producing acetic acid, comprising at least one step selected from a step that satisfies the following operating conditions (i) and a step that satisfies the following operating conditions (ii) in an acetic acid production process:

(i) operating conditions involving a hydrogen partial pressure of less than 500 kPa (absolute pressure), a carbon dioxide partial pressure of less than 70 kPa (absolute pressure), and an operating temperature of more than 175° C.; and (ii) operating conditions involving a hydrogen partial pressure of not more than 5 kPa (absolute pressure), a carbon dioxide partial pressure of less than 20 kPa (absolute pressure), and an operating temperature of more than 100° C.

The operating conditions (ii) may involve a hydrogen partial pressure of not more than 1 kPa (absolute pressure) and a carbon dioxide partial pressure of less than 2 kPa (absolute pressure).

The method for producing acetic acid according to the present invention may have a reaction step that satisfies the operating conditions (i). In this case, a reaction mixture liquid in the reaction step may have an acetic acid concentration of not less than 30% by mass and a formic acid concentration of not more than 102 ppm by mass. Also, the reaction mixture liquid in the reaction step may have an acetic acid concentration of 50 to 90% by mass, a metal catalyst concentration (in terms of the metal) of 200 to 10000 ppm by mass, a methyl iodide concentration of 1 to 20% by mass, an ionic iodide concentration of 1 to 25% by mass, a water concentration of 0.1 to 15% by mass, a methyl acetate concentration of 0.1 to 30% by mass, and a formic acid concentration of not more than 102 ppm by mass.

The method for producing acetic acid according to the present invention may have an evaporation step or a distillation step that satisfies the operating conditions (ii). A charging mixture for an evaporator in the evaporation step may have an acetic acid concentration of 50 to 90% by mass, a metal catalyst concentration (in terms of the metal) of 200 to 10000 ppm by mass, a methyl iodide concentration of 1 to 20% by mass, an ionic iodide concentration of 1 to 25% by mass, a water concentration of 0.1 to 15% by mass, a methyl acetate concentration of 0.1 to 30% by mass, and a formic acid concentration of not more than 10000 ppm by mass. Also, a charging mixture for a distillation column in the distillation step may have an acetic acid concentration of not less than 30% by mass and a formic acid concentration of not less than 5 ppm by mass. Furthermore, a charging mixture for a distillation column in the distillation step may have an acetic acid concentration of 40 to 85% by mass, a methyl iodide concentration of 2 to 50% by mass, a water concentration of 0.2 to 20% by mass, a methyl acetate concentration of 0.2 to 50% by mass, and a formic acid concentration of 5 to 10000 ppm by mass. Moreover, a charging mixture for a distillation column in the distillation step may have an acetic acid concentration of 80 to 99.9% by mass, a methyl iodide concentration of 0.01 to 16% by mass, a water concentration of 0.05 to 18% by mass, a methyl acetate concentration of 0.01 to 16% by mass, and a formic acid concentration of 5 to 10000 ppm by mass. Also, a charging mixture for a distillation column in the distillation step may have an acetic acid concentration of 99.1 to 99.999% by mass and a formic acid concentration of 5 to 9000 ppm by mass.

In the method for producing acetic acid according to the present invention, the acetic acid production process may have a carbonylation reaction step of reacting methanol with carbon monoxide to produce acetic acid, an evaporation step of separating the reaction mixture obtained in the carbonylation reaction step into a vapor stream and a residual liquid stream, a lower boiling point component removal step of separating the vapor stream by distillation into an overhead stream rich in lower boiling point component and a first acetic acid stream rich in acetic acid, or the acetic acid production process may further have at least one of the following steps (a)-(d) in addition to the carbonylation reaction step, the evaporation step, and the lower boiling point component removal step:

(a) a dehydration step of separating the first acetic acid stream by distillation into an overhead stream rich in water and a second acetic acid stream more enriched with acetic acid than the first acetic acid stream, (b) a higher boiling point component removal step of separating the first acetic acid stream or the second acetic acid stream by distillation into a bottom stream rich in higher boiling point component and a third acetic acid stream more enriched with acetic acid than the acetic acid stream before the distillation, (c) an adsorptive removal step of treating the first acetic acid stream, the second acetic acid stream, or the third acetic acid stream with an ion exchange resin to obtain a fourth acetic acid stream, and (d) a product step of distilling the first acetic acid stream, the second acetic acid stream, the third acetic acid stream or the fourth acetic acid stream to obtain a fifth acetic acid stream more enriched with acetic acid than the acetic acid stream before the distillation.

In this case, the carbonylation reaction step may satisfy the operating conditions (i). Also, at least one step selected from the evaporation step, the lower boiling point component removal step, the dehydration step, the higher boiling point component removal step, and the product step may satisfy the operating conditions (ii).

In the method for producing acetic acid according to the present invention, it is preferred that a retention time in the step that satisfies the operating conditions (i) or the step that satisfies the operating conditions (ii) should be not less than 1 minute.

In the method for producing acetic acid according to the present invention, a process solution having a formic acid concentration of not less than 10 ppm by mass may be recycled to a step that satisfies operating conditions involving a hydrogen partial pressure of less than 500 kPa (absolute pressure), a carbon dioxide partial pressure of less than 70 kPa (absolute pressure), and an operating temperature of more than 100° C.

In the method for producing acetic acid according to the present invention, the acetic acid production process may have at least one distillation step, and a column top fraction of a distillation column in the at least one distillation step may be recycled to the step that satisfies the operating conditions (i) and/or the step that satisfies the operating conditions (ii). In this case, the step to which the column top fraction of a distillation column is recycled may be the reaction step and/or the evaporation step or a distillation step positioned upstream from the distillation step associated with the distillation column.

ADVANTAGEOUS EFFECTS OF INVENTION

According to the present invention, formic acid formation can be suppressed, or formed formic acid can be efficiently decomposed, because of having a step that satisfies particular operating conditions. Therefore, a formic acid concentration in product acetic acid can be simply lowered.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

The method for producing acetic acid according to the present invention comprises at least one step selected from a step that satisfies the following operating conditions (i) and a step that satisfies the following operating conditions (ii) in an acetic acid production process:

(i) operating conditions involving a hydrogen partial pressure of less than 500 kPa (absolute pressure), a carbon dioxide partial pressure of less than 70 kPa (absolute pressure), and an operating temperature of more than 175° C.; and (ii) operating conditions involving a hydrogen partial pressure of not more than 5 kPa (absolute pressure), a carbon dioxide partial pressure of less than 20 kPa (absolute pressure), and an operating temperature of more than 100° C.

In the step that satisfies such operating conditions, formic acid formation is effectively suppressed, while formic acid in a feeding liquid for the step is efficiently decomposed. This is presumably because equilibrium reaction of $H_2+CO_2 \leftrightarrow HCOOH$ exists, and this equilibrium is shifted to the left side under the operating conditions described above. The step that satisfies the operating conditions may be any of a reaction step, an evaporation step, a distillation step, and the like.

In the present specification, the "hydrogen partial pressure" and the "carbon dioxide partial pressure" mean partial pressures of these components in a gaseous phase portion in an apparatus or equipment (a reactor, an evaporator, a distillation column, etc.) for use in the step. In the distillation column, the partial pressures in a gaseous phase portion of at least one plate (e.g., a bottom plate, a feeding plate, or an uppermost plate) can fall within the ranges described above. It is preferred that the partial pressures in a gaseous phase portion of each plate from the feeding plate to the uppermost plate should fall within the ranges described above. It is more preferred that the partial pressures in a gaseous phase portion of each plate from the bottom plate to the uppermost plate should fall within the ranges described above. The "operating temperature" means the temperature of a liquid phase portion or a gaseous phase portion in an apparatus or equipment (a reactor, an evaporator, a distillation column, etc.) for use in the step. In the distillation column, the temperature of a liquid phase portion or a gaseous phase portion of at least one plate (e.g., a bottom plate, a feeding plate, or an uppermost plate) can fall within the range described above. It is preferred that the temperature of a liquid phase portion or a gaseous phase portion of each plate from the feeding plate to the uppermost plate should fall within the range described above. It is more preferred that the temperature of a liquid phase portion or a gaseous phase portion of each plate from the bottom plate to the uppermost plate should fall within the range described above.

In the operating conditions (i), the hydrogen partial pressure (absolute pressure) can be less than 500 kPa and is preferably not more than 400 kPa, more preferably not more than 300 kPa, further preferably not more than 200 kPa, particularly preferably not more than 150 kPa. Although the lower limit of the hydrogen partial pressure (absolute pressure) is 0 kPa, the hydrogen partial pressure (absolute pressure) may be more than 1 kPa (or more than 5 kPa). The carbon dioxide partial pressure (absolute pressure) can be less than 70 kPa and is preferably not more than 60 kPa, more preferably not more than 50 kPa, further preferably not more than 40 kPa, particularly preferably not more than 30 kPa. The lower limit of the carbon dioxide partial pressure (absolute pressure) is 0 kPa, but may be 2 kPa (or 20 kPa). The operating temperature can be a temperature of more than 175° C. and is preferably not less than 178° C., more preferably not less than 181° C., further preferably not less than 184° C. The upper limit of the operating temperature is, for example, 250° C., preferably 230° C., more preferably 200° C.

In the operating conditions (ii), the hydrogen partial pressure (absolute pressure) can be not more than 5 kPa and is preferably not more than 4 kPa, more preferably not more than 3 kPa, further preferably not more than 2 kPa, particularly preferably not more than 1 kPa. The lower limit of the hydrogen partial pressure (absolute pressure) is 0 kPa. The carbon dioxide partial pressure (absolute pressure) can be less than 20 kPa and is preferably not more than 18 kPa, more preferably not more than 16 kPa, further preferably not more than 14 kPa, particularly preferably not more than 12 kPa. The lower limit of the carbon dioxide partial pressure (absolute pressure) is 0 kPa. The operating temperature can be a temperature of more than 100° C. and is preferably not less than 102° C., more preferably not less than 104° C., further preferably not less than 106° C., particularly preferably not less than 112° C. The upper limit of the operating temperature is, for example, 250° C., preferably 200° C., more preferably 175° C.

In the operating conditions (ii), the hydrogen partial pressure (absolute pressure) may be not more than 1 kPa, and the carbon dioxide partial pressure (absolute pressure) may be less than 2 kPa. In this case, the upper limit of the hydrogen partial pressure (absolute pressure) is preferably 0.9 kPa, more preferably 0.8 kPa. The lower limit of the hydrogen partial pressure (absolute pressure) is 0 kPa. The upper limit of the carbon dioxide partial pressure (absolute pressure) is preferably 1.8 kPa, more preferably 1.5 kPa, further preferably 1.0 kPa, particularly preferably 0.5 kPa. The lower limit of the carbon dioxide partial pressure (absolute pressure) is 0 kPa.

Examples of the step that satisfies the operating conditions (i) include a reaction step. In this case, it is preferred that a reaction mixture liquid in the reaction step should have an acetic acid concentration of not less than 30% by mass (e.g., 30 to 90% by mass) and a formic acid concentration of not more than 102 ppm by mass (0 to 102 ppm by mass). Further preferably, the reaction mixture liquid in the reaction step has an acetic acid concentration of 50 to 90% by mass (e.g., 60 to 80% by mass), a metal catalyst concentration (in terms of the metal) of 200 to 5000 ppm by mass (e.g., 400 to 2000 ppm by mass), a methyl iodide concentration of 1 to 20% by mass (e.g., 5 to 15% by mass), an ionic iodide concentration of 1 to 25% by mass (e.g., 5 to 20% by mass), a water concentration of 0.1 to 15% by mass (e.g., 0.8 to 10% by mass), a methyl acetate concentration of 0.1 to 30% by mass (e.g., 1 to 10% by mass), and a formic acid concentration of not more than 85 ppm by mass (0 to 85 ppm by mass).

Examples of the step that satisfies the operating conditions (ii) include an evaporation step and a distillation step. In the evaporation step that satisfies the operating conditions (ii), a charging mixture for an evaporator may have an acetic acid concentration of 50 to 90% by mass (e.g., 60 to 80% by mass), a metal catalyst concentration (in terms of the metal) of 200 to 5000 ppm by mass (e.g., 400 to 2000 ppm by mass), a methyl iodide concentration of 1 to 20% by mass (e.g., 5 to 15% by mass), an ionic iodide concentration of 1 to 25% by mass (e.g., 5 to 20% by mass), a water concentration of 0.1 to 15% by mass (e.g., 0.8 to 10% by mass), a methyl acetate concentration of 0.1 to 30% by mass (e.g., 1 to 10% by mass), and a formic acid concentration of not more than 10000 ppm by mass (e.g., 0 to 1000 ppm by mass, preferably 10 to 500 ppm by mass, further preferably 15 to 200 ppm by mass, particularly preferably 20 to 100 ppm by mass).

In the distillation step that satisfies the operating conditions (ii), a charging mixture for a distillation column may have an acetic acid concentration of not less than 30% by mass (e.g., 30 to 99.999% by mass) and a formic acid concentration of not less than 5 ppm by mass (e.g., 5 to 10000 ppm by mass). Also, in the distillation step, a charging mixture for a distillation column may have an acetic acid concentration of 40 to 85% by mass (e.g., 50 to 75% by mass), a methyl iodide concentration of 2 to 50% by mass (e.g., 5 to 30% by mass), a water concentration of 0.2 to 20% by mass (e.g., 1 to 15% by mass), a methyl acetate concentration of 0.2 to 50% by mass (e.g., 2 to 30% by mass), and a formic acid concentration of 5 to 10000 ppm by mass (e.g., 10 to 1000 ppm by mass, preferably 10 to 500 ppm by mass, further preferably 15 to 200 ppm by mass, particularly preferably 20 to 100 ppm by mass). Furthermore, in the distillation step, a charging mixture for a distillation column may have an acetic acid concentration of 80 to 99.9% by mass (e.g., 90 to 99.9% by mass, preferably 93 to 99% by mass), a methyl iodide concentration of 0.01 to 16% by mass (e.g., 0.1 to 8% by mass, preferably 0.2 to 5% by mass), a water concentration of 0.05 to 18% by mass (e.g., 0.1 to 8% by mass, preferably 0.2 to 5% by mass), a methyl acetate concentration of 0.01 to 16% by mass (e.g., 0.1 to 8% by mass, preferably 0.2 to 5% by mass), and a formic acid concentration of 5 to 10000 ppm by mass (e.g., 10 to 1000 ppm by mass, preferably 10 to 500 ppm by mass, further preferably 15 to 200 ppm by mass, particularly preferably 20 to 100 ppm by mass). Moreover, in the distillation step, a charging mixture for a distillation column may have an acetic acid concentration of 99.1 to 99.999% by mass and a formic acid concentration of 5 to 9000 ppm by mass (e.g., 10 to 1000 ppm by mass, preferably 10 to 500 ppm by mass, further preferably 15 to 200 ppm by mass, particularly preferably 20 to 100 ppm by mass).

In the method for producing acetic acid, the acetic acid production process may have a carbonylation reaction step of reacting methanol with carbon monoxide to produce acetic acid, an evaporation step of separating the reaction mixture obtained in the carbonylation reaction step into a vapor stream and a residual liquid stream, a lower boiling point component removal step of separating the vapor stream by distillation into an overhead stream rich in lower boiling point component and a first acetic acid stream rich in acetic acid, and a dehydration step of separating the first acetic acid stream by distillation into an overhead stream rich in water and a second acetic acid stream more enriched with acetic acid than the first acetic acid stream. Alternatively, in addition to the steps, the acetic acid production process may further have at least one of the following steps (a)-(d) in addition to the carbonylation reaction step, the evaporation step, and the lower boiling point component removal step:
(a) a dehydration step of separating the first acetic acid stream by distillation into an overhead stream rich in water and a second acetic acid stream more enriched with acetic acid than the first acetic acid stream,
(b) a higher boiling point component removal step of separating the first acetic acid stream or the second acetic acid stream by distillation into a bottom stream rich in higher boiling point component and a third acetic acid stream more enriched with acetic acid than the acetic acid stream before the distillation,
(c) an adsorptive removal step of treating the first acetic acid stream, the second acetic acid stream, or the third acetic acid stream with an ion exchange resin to obtain a fourth acetic acid stream, and
(d) a product step of distilling the first acetic acid stream, the second acetic acid stream, the third acetic acid stream or the fourth acetic acid stream to obtain a fifth acetic acid stream more enriched with acetic acid than the acetic acid stream before the distillation.

The carbonylation reaction step may satisfy the operating conditions (i). Also, at least one step selected from the evaporation step, the lower boiling point component removal step, the dehydration step, the higher boiling point component removal step, and the product step (preferably the lower boiling point component removal step, further preferably the lower boiling point component removal step and the dehydration step, alternatively the evaporation step and the lower boiling point component removal step, particularly preferably the evaporation step, lower boiling point component removal step, and the dehydration step) may satisfy the operating conditions (ii).

In the method for producing acetic acid according to the present invention, it is preferred that a retention time in the step that satisfies the operating conditions (i) or (ii) should be not less than 1 minute (e.g., not less than 5 minutes, particularly, not less than 10 minutes). The upper limit of the retention time is, for example, 2 hours, preferably 1 hour. Formic acid contained in the system can be securely decomposed by retention for the predetermined time under the operating conditions (i) or (ii).

In the method for producing acetic acid according to the present invention, a process solution having a formic acid concentration of not less than 10 ppm by mass (e.g., 10 to 10000 ppm by mass, preferably 15 to 1000 ppm by mass, further preferably 20 to 200 ppm by mass) may be recycled to the step that satisfies the operating conditions (i) and/or the step that satisfies the operating conditions (ii) (e.g., the reaction step, the evaporation step, the lower boiling point component removal step, or the dehydration step). Formic acid in such a process solution can be efficiently decomposed by recycling the process solution to the step.

In the method for producing acetic acid according to the present invention, the acetic acid production process may have at least one distillation step, and a column top fraction of a distillation column in the at least one distillation step may be recycled to the step that satisfies the operating conditions (i) and/or the step that satisfies the operating conditions (ii). Examples of the step that satisfies the operating conditions (i) and the step that satisfies the operating conditions (ii) include the reaction step, the evaporation step, the lower boiling point component removal step, and the dehydration step. In this case, it is preferred that the step to which the column top fraction of a distillation column is recycled should be the reaction step or should be the evaporation step or a distillation step positioned upstream from the distillation step associated with the distillation column. Because formic acid has a lower boiling point than that of acetic acid and is therefore concentrated at the column top, a column top fraction of the distillation column is recycled to the step that satisfies the operating conditions (i) and/or the step that satisfies the operating conditions (ii) so that formic acid in the column top fraction can be efficiently decomposed.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. In the present invention, the steps are not limited to those described above and may exclude, particularly, equipment of the distillation column 5, the distillation column (higher boiling point component removal column) 6, the ion exchange resin column 7, the acetaldehyde separation and removal system 9 (acetaldehyde removal column, etc.). As mentioned later, a product column may be disposed downstream of the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \qquad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11. Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^{3-}$ can be used as the rhodium catalyst. For example, an iridium complex represented by the chemical formula $[Ir(CO)_3I_3]^-$ can be used as the iridium catalyst. A metal complex catalyst is preferred as the metal catalyst. The concentration (in terms of the metal) of the catalyst in the reaction mixture is, for example, 200 to 10000 ppm by mass, preferably 300 to 5000 ppm by mass, further preferably 400 to 2000 ppm by mass, with respect to the whole liquid phase (reaction mixture liquid) of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass (preferably 5 to 15% by mass) with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. In addition, when an iridium catalyst or the like is used, for example, a ruthenium compound or an osmium compound can be used as a co-catalyst. The amount of these compounds to be used as the total amount is, for example 0.1 to 30 moles (in terms of metal), preferably 0.5 to 15 moles (in terms of metal) based on 1 mole of iridium (in terms of metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, propionic acid, and alkyl iodides such as hexyl iodide and decyl iodide. Also, the reaction mixture may contain a metal, such as iron, nickel, chromium, manganese, or molybdenum, generated by the corrosion of the apparatus (hereinafter, also referred to as a "corroded metal"), and other metals such as cobalt, zinc, and copper. The corroded metal and other metals are also collectively referred to as a "corroded metal, etc.". The total content of these impurities such as by-products and corroded metals is, for example, 1 ppm by mass to 1% by mass with respect to the whole liquid phase of the reaction mixture. Thus, the process solution in this acetic acid production process may contain, for example, approximately 1 ppm by mass to 1% by mass in total of the impurities. The concentration of the formic acid in the reaction mixture is, for example, 0 to 102 ppm by mass, preferably 0 to 85 ppm by mass, further preferably 0 to 50 ppm by mass, with respect to the whole liquid phase of the reaction mixture.

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.5 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

In the present invention, it is preferred that the reaction step using the reaction vessel 1 should satisfy the operating conditions (i) involving a hydrogen partial pressure of less than 500 kPa (absolute pressure), a carbon dioxide partial pressure of less than 70 kPa (absolute pressure), and an operating temperature of more than 175° C. In this case, the hydrogen partial pressure (absolute pressure) can be less than 500 kPa and is preferably not more than 400 kPa, more preferably not more than 300 kPa, further preferably not more than 200 kPa, particularly preferably not more than 150 kPa. Although the lower limit of the hydrogen partial pressure (absolute pressure) is 0 kPa, the hydrogen partial pressure (absolute pressure) may be more than 1 kPa (or more than 5 kPa). The carbon dioxide partial pressure (absolute pressure) can be less than 70 kPa and is preferably not more than 60 kPa, more preferably not more than 50 kPa, further preferably not more than 40 kPa, particularly preferably not more than 30 kPa. The lower limit of the carbon dioxide partial pressure (absolute pressure) is 0 kPa, but may be 2 kPa (or 20 kPa). The operating temperature can be a temperature of more than 175° C. and is preferably not less than 178° C., more preferably not less than 181° C., further preferably not less than 184° C. The upper limit of the operating temperature is, for example, 250° C., preferably 230° C., more preferably 200° C. The reaction step using the reaction vessel 1 satisfies the operating conditions (i), whereby formic acid formation in the reaction vessel 1 is suppressed. Furthermore, when a liquid containing formic acid is introduced to the reaction vessel 1, the formic acid is efficiently decomposed.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, and propionic acid and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The acetic acid concentration of the vapor stream is, for example, 50 to 85% by mass, preferably 55 to 75% by mass. The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

In the present invention, it is preferred that the evaporation step using the evaporator 2 should satisfy the operating conditions (ii) involving a hydrogen partial pressure of not more than 5 kPa (absolute pressure), a carbon dioxide partial pressure of less than 20 kPa (absolute pressure), and an operating temperature of more than 100° C. In this case, the hydrogen partial pressure (absolute pressure) is preferably not more than 4 kPa, more preferably not more than 3 kPa, further preferably not more than 1 kPa, particularly preferably not more than 0.8 kPa. The lower limit of the hydrogen partial pressure (absolute pressure) is 0 kPa. The carbon dioxide partial pressure (absolute pressure) is preferably not more than 12 kPa, more preferably 8 kPa, further preferably not more than 3 kPa, particularly preferably not more than 1 kPa. The lower limit of the carbon dioxide partial pressure (absolute pressure) is 0 kPa. The operating temperature is preferably not less than 112° C., more preferably not less than 120° C., further preferably not less than 130° C. The upper limit of the operating temperature is, for example, 260° C., preferably 200° C., more preferably 180° C. (or 170° C. or 160° C.).

In the evaporation step that satisfies the operating conditions (ii), the charging mixture for the evaporator 2 may have an acetic acid concentration of, for example, 50 to 90% by mass (preferably 60 to 80% by mass), a metal catalyst concentration (in terms of the metal) of, for example, 200 to 10000 ppm by mass (preferably 300 to 5000 ppm by mass, further preferably 400 to 2000 ppm by mass), a methyl iodide concentration of, for example, 1 to 20% by mass (preferably 5 to 15% by mass), an ionic iodide concentration of, for example, 1 to 25% by mass (preferably 5 to 20% by mass), a water concentration of, for example, 0.1 to 15% by mass (preferably 0.8 to 10% by mass), a methyl acetate concentration of, for example, 0.1 to 30% by mass (preferably 1 to 10% by mass), and a formic acid concentration of, for example, not more than 10000 ppm by mass (preferably 0 to 1000 ppm by mass, more preferably 10 to 500 ppm by mass, further preferably 15 to 200 ppm by mass, particularly preferably 20 to 100 ppm by mass). The evaporation step using the evaporator 2 satisfies the operating conditions, whereby formic acid formation in the evaporator 2 is suppressed. Furthermore, when a liquid containing formic acid is introduced to the evaporator 2, the formic acid is efficiently decomposed.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.).

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51.

In the present invention, it is preferred that the distillation step using the distillation column (lower boiling point component removal column) 3 should satisfy the operating conditions (ii) involving a hydrogen partial pressure of not more than 5 kPa (absolute pressure), a carbon dioxide partial pressure of less than 20 kPa (absolute pressure), and an operating temperature of more than 100° C. In this case, the hydrogen partial pressure (absolute pressure) is preferably not more than 4 kPa, more preferably not more than 3 kPa, further preferably not more than 1 kPa. The lower limit of the hydrogen partial pressure (absolute pressure) is 0 kPa. The carbon dioxide partial pressure (absolute pressure) is preferably not more than 12 kPa, more preferably not more than 8 kPa, further preferably not more than 3 kPa, particularly preferably not more than 1 kPa. The lower limit of the carbon dioxide partial pressure (absolute pressure) is 0 kPa. The operating temperature is preferably not less than 112° C., more preferably not less than 114° C. The upper limit of the operating temperature is, for example, 165° C., preferably 160° C., more preferably 150° C. (or 140° C. or 130° C.).

In the case where the distillation step using the distillation column (lower boiling point component removal column) 3 satisfies the operating conditions (ii), the charging mixture for the distillation column 3 may have an acetic acid concentration of not less than 30% by mass (e.g., 30 to 99.999% by mass) and a formic acid concentration of not less than 5 ppm by mass (e.g., 5 to 10000 ppm by mass). Also, the charging mixture for the distillation column 3 has an acetic acid concentration of preferably 40 to 85% by mass (e.g., 50 to 85% by mass), further preferably 50 to 75% by mass (e.g., 55 to 75% by mass), a methyl iodide concentration of preferably 2 to 50% by mass (e.g., 5 to 30% by mass), a water concentration of preferably 0.2 to 20% by mass (e.g., 1 to 15% by mass), a methyl acetate concentration of preferably 0.2 to 50% by mass (e.g., 2 to 30% by mass), and a formic acid concentration of preferably 5 to 10000 ppm by mass (e.g., 10 to 1000 ppm by mass, more preferably 10 to 500 ppm by mass, particularly, 15 to 200 ppm by mass, in particular, 20 to 100 ppm by mass). The distillation step using the distillation column 3 satisfies the operating conditions (ii), whereby formic acid formation in the distillation column 3 is suppressed. In addition, when a liquid containing formic acid is fed to the distillation column 3, the formic acid is efficiently decomposed.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91*a*. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93*a*. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91*a* or 93*a* (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91*a*. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93*a*. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91*a* or 93*a* (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation.

The vapor at the column top is led to a condenser 98a through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94a through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94a, 97a, or 98a (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream may contain, in addition to acetic acid, for example, methyl iodide, hydrogen iodide, water, methyl acetate, dimethyl ether, methanol, acetaldehyde, formic acid, and propionic acid. The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The first acetic acid stream withdrawn as a side stream from the distillation column 3, column bottom fraction of the distillation column 3, or condensate of the vapor in the column bottom of the distillation column 3 may be directly used as product acetic acid, or may be directly and continuously introduced into the distillation column 6 without using the distillation column 5.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. The distillation column 5 consists of, for example, a distillation column such as a plate column or a packed column. In the case of adopting a plate column as the distillation column 5, the theoretical number of plates thereof is, for example, 5 to 50, and the reflux ratio is, for example, 0.2 to 3000 according to the theoretical number of plates. In the inside of the distillation column 5 in the second distillation step, the column top pressure is set to, for example, 150 to 250 kPa (gauge pressure), and the column bottom pressure is higher than the column top pressure and is set to, for example, 160 to 290 kPa (gauge pressure). In the inside of the distillation column 5 in the second distillation step, the column top temperature is, for example, a temperature of higher than the boiling point of water and lower than the boiling point of acetic acid at the set column top pressure and is set to 130 to 160° C., and the column bottom temperature is, for example, a temperature of not less than the boiling point of acetic acid at the set column bottom pressure and is set to 150 to 175° C.

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5 and contains, for example, propionic acid, potassium acetate (in the case of feeding potassium hydroxide to the line 27, etc.), and the entrained catalyst and co-catalyst mentioned above. This bottom fraction may also contain acetic acid. Such a bottom fraction is continuously introduced in the form of the second acetic acid stream to the next distillation column 6 through the line 34.

In the present invention, it is preferred that the distillation step using the distillation column (dehydration column) 5 should satisfy the operating conditions (ii) involving a hydrogen partial pressure of not more than 5 kPa (absolute pressure), a carbon dioxide partial pressure of less than 20 kPa (absolute pressure), and an operating temperature of more than 100° C. In this case, the hydrogen partial pressure (absolute pressure) is preferably not more than 2 kPa, more preferably not more than 1 kPa, further preferably not more than 0.5 kPa. The lower limit of the hydrogen partial pressure (absolute pressure) is 0 kPa. The carbon dioxide partial pressure (absolute pressure) is preferably not more than 5 kPa, more preferably not more than 2 kPa, further preferably not more than 1 kPa (e.g., not more than 0.5 kPa). The lower limit of the carbon dioxide partial pressure (absolute pressure) is 0 kPa. The operating temperature is preferably not less than 120° C., more preferably not less than 130° C. The upper limit of the operating temperature is, for example, 170° C., preferably 165° C., more preferably 160° C., further preferably 155° C.

In the case where the distillation step using the distillation column (dehydration column) 5 satisfies the operating conditions (ii), the charging mixture for the distillation column 5 may have an acetic acid concentration of not less than 30% by mass (e.g., 30 to 99.999% by mass) and a formic acid concentration of not less than 5 ppm by mass (e.g., 5 to 10000 ppm by mass). Also, the charging mixture for the distillation column 5 has an acetic acid concentration of preferably 80 to 99.9% by mass (e.g., 90 to 99.9% by mass, particularly, 93 to 99% by mass), a methyl iodide concentration of preferably 0.01 to 16% by mass (e.g., 0.1 to 8% by mass, particularly, 0.2 to 5% by mass), a water concentration of preferably 0.05 to 18% by mass (e.g., 0.1 to 8% by mass, particularly, 0.2 to 5% by mass), a methyl acetate concentration of preferably 0.01 to 16% by mass (e.g., 0.1 to 8% by mass, particularly, 0.2 to 5% by mass), and a formic acid concentration of preferably 5 to 10000 ppm by mass (e.g., 10 to 1000 ppm by mass, more preferably 10 to 500 ppm by mass, particularly, 15 to 200 ppm by mass, in particular, 20 to 100 ppm by mass). The distillation step using the distillation column 5 satisfies the operating conditions (ii), whereby formic acid formation in the distillation column 5 is suppressed. In addition, when a liquid containing formic acid is fed to the distillation column 5, the formic acid is efficiently decomposed.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains, for example, propionic acid and potassium acetate (in the case of feeding potassium hydroxide to the line 34, etc.). Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

In the present invention, it is preferred that the distillation step using the distillation column (higher boiling point component removal column) 6 should satisfy the operating conditions (ii) involving a hydrogen partial pressure of not more than 5 kPa (absolute pressure), a carbon dioxide partial pressure of less than 20 kPa (absolute pressure), and an operating temperature of more than 100° C. In this case, the hydrogen partial pressure (absolute pressure) is preferably not more than 2 kPa, more preferably not more than 1 kPa, further preferably not more than 0.5 kPa. The lower limit of the hydrogen partial pressure (absolute pressure) is 0 kPa. The carbon dioxide partial pressure (absolute pressure) is preferably not more than 5 kPa, more preferably not more than 2 kPa, further preferably not more than 1 kPa (e.g., not more than 0.5 kPa). The lower limit of the carbon dioxide partial pressure (absolute pressure) is 0 kPa. The operating temperature is preferably not less than 120° C., more preferably not less than 130° C. The upper limit of the operating temperature is, for example, 165° C., preferably 160° C., further preferably 155° C.

In the case where the distillation step using the distillation column (higher boiling point component removal column) 6 satisfies the operating conditions (ii), the charging mixture for the distillation column 6 has an acetic acid concentration of preferably 99.1 to 99.99% by mass and a formic acid concentration of preferably 5 to 9000 ppm by mass (e.g., 10 to 1000 ppm by mass, more preferably 10 to 500 ppm by mass, particularly, 15 to 200 ppm by mass, in particular, 20 to 100 ppm by mass). The distillation step using the distillation column 6 satisfies the operating conditions (ii), whereby formic acid formation in the distillation column 6 is suppressed. In addition, when a liquid containing formic acid is fed to the distillation column 6, the formic acid is efficiently decomposed.

The ion exchange resin column 7 is a purification unit for performing the adsorptive removal step. This adsorptive removal step is a step for further purifying acetic acid by the adsorptive removal of, mainly, alkyl iodides (hexyl iodide, decyl iodide, etc.) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m$^3$ resin volume (m$^3$/h)] is, for example, 3 to 15 m$^3$/h·m$^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

In the present invention, it is preferred that the distillation step using the distillation column (product column) should satisfy the operating conditions (ii) involving a hydrogen partial pressure of not more than 5 kPa (absolute pressure), a carbon dioxide partial pressure of less than 20 kPa (absolute pressure), and an operating temperature of more than 100° C. In this case, the hydrogen partial pressure (absolute pressure) is preferably not more than 2 kPa, more preferably not more than 1 kPa, further preferably not more than 0.5 kPa. The lower limit of the hydrogen partial pressure (absolute pressure) is 0 kPa. The carbon dioxide partial pressure (absolute pressure) is preferably not more than 5 kPa, more preferably not more than 2 kPa, further preferably not more than 1 kPa (e.g., not more than 0.5 kPa). The lower limit of the carbon dioxide partial pressure (absolute pressure) is 0 kPa. The operating temperature is preferably not less than 120° C., more preferably not less than 130° C. The upper limit of the operating temperature is, for example, 165° C., preferably 160° C., more preferably 155° C.

In the case where the distillation step using the distillation column (product column) satisfies the operating conditions (ii), the charging mixture for the distillation column (product column) has an acetic acid concentration of preferably 99.8 to 99.999% by mass and a formic acid concentration of preferably 5 to 2000 ppm by mass (e.g., 5 to 1000 ppm by mass, particularly, 5 to 100 ppm by mass). The distillation step using the distillation column (product column) satisfies the operating conditions (ii), whereby formic acid formation in the distillation column (product column) is suppressed. In addition, when a liquid containing formic acid is fed to the distillation column (product column), the formic acid is efficiently decomposed.

In the embodiments described above, it is preferred that, as mentioned above, the retention time in the step that satisfies the operating conditions (i) or the step that satisfies the operating conditions (ii) should be not less than 1 minute (e.g., not less than 5 minutes, particularly, not less than 10 minutes). The upper limit of the retention time is, for example, 2 hours, preferably 1 hour.

Also, a process solution having a formic acid concentration of not less than 10 ppm by mass (e.g., 10 to 10000 ppm by mass, preferably 15 to 1000 ppm by mass, further preferably 20 to 200 ppm by mass) may be recycled to a step that satisfies (iii) operating conditions involving a hydrogen partial pressure of less than 500 kPa (absolute pressure), a carbon dioxide partial pressure of less than 70 kPa (absolute pressure), and an operating temperature of more than 100° C. Examples of the step that satisfies the operating conditions (iii) include the reaction step, the evaporation step, and the distillation steps (e.g., the lower boiling point component removal step and the dehydration step). The step that satisfies the operating conditions (iii) includes the step that satisfies the operating conditions (i) and the step that satisfies the operating conditions (ii). The process solution having a formic acid concentration of not less than 10 ppm by mass) is recycled to the step that satisfies the operating conditions (iii) so that the formic acid contained in the process solution is efficiently decomposed in this step.

Furthermore, a column top fraction of the distillation column in at least one distillation step, for example, the lower boiling point component removal step, the dehydration step, the higher boiling point component removal step, or the product step may be recycled to the step that satisfies the operating conditions (i) or the step that satisfies the operating conditions (ii). Examples of the step that satisfies the operating conditions (i) and the step that satisfies the operating conditions (ii) include the reaction step, the evaporation step, the lower boiling point component removal step, and the dehydration step. In this case, it is preferred that the step to which the column top fraction of the distillation column is recycled should be the reaction step or should be the evaporation step or a distillation step (e.g., the lower boiling point component removal step, the dehydration step, or the higher boiling point component removal step) positioned upstream from the distillation step associated with the distillation column.

EXAMPLES

Hereinafter, the present invention will be described in more detail with reference to Examples. However, the present invention is not intended to be limited by these Examples. "MeI" represents methyl iodide, and "MA" represents methyl acetate. In the compositional analysis of a liquid phase portion, a water concentration was measured by the Karl Fischer water determination method; a formic acid concentration was measured by liquid chromatography; a rhodium concentration was measured by ICP analysis (or atomic adsorption analysis); as for a lithium iodide concentration, Li was measured by ICP analysis, and iodine was measured by electrometric titration analysis; and concentrations of other components were measured by gas chromatography. The partial pressure of each gaseous component in a gaseous phase portion was calculated from total pressure and each gaseous component concentration measured by gas chromatography. The units "%" and "ppm" mean "% by mass" and "ppm by mass", respectively.

Comparative Example 1

10% of MeI, 4% of MA, 2.5% of water, 15% of LiI, 500 ppm (in terms of the metal) of a rhodium complex catalyst ($[Rh(CO)_2I_2]^-$), and acetic acid as a balance were fed as raw materials in initial introduction composition to a 1000 ml zirconium autoclave. After purging with $N_2$ (holding at $N_2$ atmospheric pressure), $H_2$, $CO_2$, and CO were fed to the autoclave to make a $H_2$ partial pressure of 510 kPa (absolute pressure), a $CO_2$ partial pressure of 70 kPa (absolute pressure), and a CO partial pressure of 1.6 MPa (absolute pressure). The autoclave was held for 30 minutes with the temperature kept at 180° C. in an oil bath. After cooling, the liquid was sampled and subjected to compositional analysis. As a result, the formic acid concentration was 88 ppm.

Although the MA concentration was decreased to 0.1%, there was no large change in the composition of the other components. Results of compositional analysis at the start of the experiment, after 8 minutes into the experiment, and at the completion of the experiment, and the formic acid concentration at the completion of the experiment are shown in the table below.

Comparative Example 2

The same experiment as in Comparative Example 1 was conducted except that: 10% of MeI, 5% of MA, 2.5% of water, 15% of LiI, 500 ppm (in terms of the metal) of a rhodium complex catalyst ($[Rh(CO)_2I_2]^-$), and acetic acid as a balance were fed as the initial introduction composition; $H_2$, $CO_2$, and CO were fed to the autoclave to make a $H_2$ partial pressure of 510 kPa (absolute pressure), a $CO_2$ partial pressure of 70 kPa (absolute pressure), and a CO partial pressure of 1.5 MPa (absolute pressure); and the autoclave was held at a temperature of 170° C. for 30 minutes. After cooling, the liquid was sampled and subjected to compositional analysis. As a result, the formic acid concentration was 102 ppm. Although the MA concentration was decreased to 0.1%, there was no large change in the composition of the other components. Results of compositional analysis at the start of the experiment and after 9 minutes into the experiment, and the formic acid concentration at the completion of the experiment are shown in the table below.

Comparative Example 3

The same experiment as in Comparative Example 1 was conducted except that: 40% of MeI, 5% of MA, 2% of water, 52 ppm of formic acid, and acetic acid as a balance were fed as the initial introduction composition; $H_2$, $CO_2$, and CO were fed to the autoclave to make a $H_2$ partial pressure of 5 kPa (absolute pressure), a $CO_2$ partial pressure of 10 kPa (absolute pressure), and a CO partial pressure of 20 kPa (absolute pressure); and the autoclave was held at a temperature of 100° C. for 30 minutes. After cooling, the liquid was sampled and subjected to compositional analysis. As a result, the formic acid concentration was 49 ppm. Since no catalyst was added, carbonylation reaction did not occur so that there was no change in the basic composition except for formic acid. Results of compositional analysis at the start of the experiment and at the completion of the experiment, and the formic acid concentration at the completion of the experiment are shown in the table below.

Comparative Example 4

The same experiment as in Comparative Example 1 was conducted except that: 50% of water, 5% of MeI, 5% of MA, 50 ppm of formic acid, and acetic acid as a balance were fed as the initial introduction composition; $H_2$, $CO_2$, and CO were fed to the autoclave to make a $H_2$ partial pressure of 5 kPa (absolute pressure), a $CO_2$ partial pressure of 2 kPa (absolute pressure), and a CO partial pressure of 10 kPa (absolute pressure); and the autoclave was held at a temperature of 100° C. for 30 minutes. After cooling, the liquid was sampled and subjected to compositional analysis. As a result, the formic acid concentration was 48 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Comparative Example 5

The same experiment as in Comparative Example 1 was conducted except that: 0.2% of water, 51 ppm of formic acid, and acetic acid as a balance were fed as the initial introduction composition; $H_2$, $CO_2$, and CO were fed to the autoclave to make a $H_2$ partial pressure of 1 kPa (absolute pressure), a $CO_2$ partial pressure of 1 kPa (absolute pressure), and a CO partial pressure of 10 kPa (absolute pressure); and the autoclave was held at a temperature of 100° C. for 30 minutes. After cooling, the liquid was sampled and subjected to compositional analysis. As a result, the formic acid concentration was 50 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Comparative Example 6

The same experiment as in Comparative Example 1 was conducted except that: 1.0% of MeI, 1.1% of MA, 2.3% of water, 19.5% of LiI, 670 ppm (in terms of the metal) of a rhodium complex catalyst ($[Rh(CO)_2I_2]^-$), 50 ppm of formic acid, and acetic acid as a balance were fed as the initial introduction composition; $H_2$, $CO_2$, and CO were fed to the autoclave to make a $H_2$ partial pressure of 5.3 kPa (absolute pressure), a $CO_2$ partial pressure of 23 kPa (absolute pressure), and a CO partial pressure of 0.004 MPa (absolute pressure); and the autoclave was held at a temperature of 145° C. for 5 minutes. After cooling, the liquid was sampled and subjected to compositional analysis. As a result, the formic acid concentration was 49 ppm. The MA concentration was 1.0% and was thus hardly changed. There was no large change in the composition of the other components. Results of compositional analysis at the start of the experiment, and the formic acid concentration at the completion of the experiment are shown in the table below.

Example 1

The same experiment as in Comparative Example 1 was conducted except that: 10% of MeI, 4% of MA, 2.5% of water, 15% of LiI, 500 ppm (in terms of the metal) of a rhodium complex catalyst ($[Rh(CO)_2I_2]^-$), and acetic acid as a balance were fed as the initial introduction composition; and $H_2$, $CO_2$, and CO were fed to the autoclave to make a $H_2$ partial pressure of 105 kPa (absolute pressure), a $CO_2$ partial pressure of 69 kPa (absolute pressure), and a CO partial pressure of 1.6 MPa (absolute pressure). After cooling, the liquid was sampled and subjected to compositional analysis. As a result, the formic acid concentration was 48 ppm. Although the MA concentration was decreased to 0.1%, there was no large change in the composition of the other components. Results of compositional analysis at the start of the experiment and after 8 minutes into the experiment, and the formic acid concentration at the completion of the experiment are shown in the table below.

Example 2

The same experiment as in Example 1 was conducted except that: 10% of MeI, 4% of MA, 2% of water, 15% of LiI, 500 ppm (in terms of the metal) of a rhodium complex catalyst ([Rh(CO)$_2$I$_2$]$^-$), and acetic acid as a balance were fed as the initial introduction composition; and H$_2$, CO$_2$, and CO were fed to the autoclave to make a H$_2$ partial pressure of 50 kPa (absolute pressure), a CO$_2$ partial pressure of 65 kPa (absolute pressure), and a CO partial pressure of 1.6 MPa (absolute pressure). After cooling, the liquid was sampled and subjected to compositional analysis. As a result, the formic acid concentration was 35 ppm. Although the MA concentration was decreased to 0.1%, there was no large change in the composition of the other components. Results of compositional analysis at the start of the experiment and after 6 minutes into the experiment, and the formic acid concentration at the completion of the experiment are shown in the table below.

Example 3

The same experiment as in Example 1 was conducted except that: 10% of MeI, 4% of MA, 2% of water, 15% of LiI, 500 ppm (in terms of the metal) of a rhodium complex catalyst ([Rh(CO)$_2$I$_2$]$^-$), and acetic acid as a balance were fed as the initial introduction composition; and H$_2$, CO$_2$, and CO were fed to the autoclave to make a H$_2$ partial pressure of 20 kPa (absolute pressure), a CO$_2$ partial pressure of 60 kPa (absolute pressure), and a CO partial pressure of 1.6 MPa (absolute pressure). After cooling, the liquid was sampled and subjected to compositional analysis. As a result, the formic acid concentration was 28 ppm. Although the MA concentration was decreased to 0.1%, there was no large change in the composition of the other components. Results of compositional analysis at the start of the experiment and after 5 minutes into the experiment, and the formic acid concentration at the completion of the experiment are shown in the table below.

Example 4

The same experiment as in Comparative Example 1 was conducted except that the autoclave was held at a temperature of 188° C. for 30 minutes. After cooling, the liquid was sampled and subjected to compositional analysis. As a result, the formic acid concentration was 21 ppm. Although the MA concentration was decreased to 0.1%, there was no large change in the composition of the other components. Results of compositional analysis at the start of the experiment and after 8 minutes into the experiment, and the formic acid concentration at the completion of the experiment are shown in the table below.

Example 5

The same experiment as in Comparative Example 3 was conducted except that the autoclave was held at a temperature of 110° C. for 30 minutes. After cooling, the liquid was sampled and subjected to compositional analysis. As a result, the formic acid concentration was 45 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 6

The same experiment as in Comparative Example 4 was conducted except that the autoclave was held at a temperature of 110° C. for 30 minutes. After cooling, the liquid was sampled and subjected to compositional analysis. As a result, the formic acid concentration was 43 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 7

The same experiment as in Comparative Example 5 was conducted except that the autoclave was held at a temperature of 110° C. for 30 minutes. After cooling, the liquid was sampled and subjected to compositional analysis. As a result, the formic acid concentration was 44 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 8

The same experiment as in Comparative Example 3 was conducted except that the autoclave was held at a temperature of 120° C. for 30 minutes. After cooling, the liquid was sampled and subjected to compositional analysis. As a result, the formic acid concentration was 38 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 9

The same experiment as in Comparative Example 4 was conducted except that the autoclave was held at a temperature of 120° C. for 30 minutes. After cooling, the liquid was sampled and subjected to compositional analysis. As a result, the formic acid concentration was 32 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 10

The same experiment as in Comparative Example 5 was conducted except that the autoclave was held at a temperature of 120° C. for 30 minutes. After cooling, the liquid was sampled and subjected to compositional analysis. As a result, the formic acid concentration was 36 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 11

The same experiment as in Comparative Example 5 was conducted except that: in the initial introduction composition, the water concentration was changed to 0.1%, and the formic acid concentration was changed to 52 ppm; and the autoclave was held at a temperature of 140° C. for 30 minutes. After cooling, the liquid was sampled and subjected to compositional analysis. As a result, the formic acid concentration was 22 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 12

The same experiment as in Comparative Example 5 was conducted except that: in the initial introduction composition, the water concentration was changed to 0.1%, and the formic acid concentration was changed to 52 ppm; and the autoclave was held at a temperature of 150° C. for 30 minutes. After cooling, the liquid was sampled and subjected to compositional analysis. As a result, the formic acid concentration was 13 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 13

The same experiment as in Comparative Example 5 was conducted except that: in the initial introduction composition, the water concentration was changed to 0.1%, and the formic acid concentration was changed to 52 ppm; no CO was fed; and the autoclave was held at a temperature of 150° C. for 30 minutes. After cooling, the liquid was sampled and subjected to compositional analysis. As a result, the formic acid concentration was 15 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 14

The same experiment as in Comparative Example 4 was conducted except that: the initial introduction composition was changed to 5% of MeI, 5% of MA, 5% of water, 50 ppm of formic acid, and acetic acid as a balance; and the autoclave was held at a temperature of 150° C. for 30 minutes. After cooling, the liquid was sampled and subjected to compositional analysis. As a result, the formic acid concentration was 17 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 15

The same experiment as in Example 8 was conducted except that $H_2$, $CO_2$, and CO were fed to the autoclave to make a $H_2$ partial pressure of 0.5 kPa (absolute pressure), a $CO_2$ partial pressure of 0.3 kPa (absolute pressure), and a CO partial pressure of 4 kPa (absolute pressure). After cooling, the liquid was sampled and subjected to compositional analysis. As a result, the formic acid concentration was 31 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 16

The same experiment as in Example 15 was conducted except that the retention time was changed to 5 minutes. After cooling, the liquid was sampled and subjected to compositional analysis. As a result, the formic acid concentration was 39 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 17

The same experiment as in Example 15 was conducted except that the retention time was changed to 2 minutes. After cooling, the liquid was sampled and subjected to compositional analysis. As a result, the formic acid concentration was 44 ppm. Since no catalyst was added, carbonylation reaction did not occur so that there was no change in the basic composition except for formic acid. Results of compositional analysis at the start of the experiment, and the formic acid concentration at the completion of the experiment are shown in the table below.

Example 18

The same experiment as in Comparative Example 6 was conducted except that $H_2$, $CO_2$, and CO were fed to the autoclave to make a $H_2$ partial pressure of 1.2 kPa (absolute pressure), a $CO_2$ partial pressure of 0.5 kPa (absolute pressure), and a CO partial pressure of 0.004 MPa (absolute pressure). After cooling, the liquid was sampled and subjected to compositional analysis. As a result, the formic acid concentration was 38 ppm. The MA concentration was 1.0% and was thus hardly changed. There was no large change in the composition of the other components. Results of compositional analysis at the start of the experiment, and the formic acid concentration at the completion of the experiment are shown in the table below.

The conditions and results of Comparative Examples and Examples are shown in Tables 1 and 2. In Tables 1 and 2, "PH2" represents a hydrogen partial pressure, "PCO2" represents a carbon dioxide partial pressure, and "PCO" represents a carbon monoxide partial pressure. In the tables, "balance" is described about the acetic acid concentration. In actuality, the sampled solution may contain 1 ppm to 1% in total of impurities such as by-products mentioned in the section described about the reaction mixture.

TABLE 1

| | | Comparative Examples | | | | | | | | | |
|---|---|---|---|---|---|---|---|---|---|---|---|
| | | 1 | | | 2 | | 3 | | 4 | 5 | 6 |
| | | Start | 8 min later | Completion | Start | 9 min later | Start | Completion | Start | Start | Start |
| Formic acid | ppm by mass | 0 | 75 | 88 | 0 | 89 | 52 | 49 | 50 | 51 | 50 |
| Mel | % by mass | 10.1 | 9.9 | 9.8 | 10.3 | 9.9 | 40.5 | 40.3 | 5.2 | 0 | 1 |
| MA | % by mass | 4.1 | 3.1 | 0.1 | 4.8 | 3.5 | 5.2 | 5.2 | 4.9 | 0 | 1.1 |
| Water | % by mass | 2.5 | 2.3 | 1.5 | 2.6 | 2.3 | 2.1 | 2.1 | 50.5 | 0.2 | 2.3 |
| LiI | % by mass | 15 | 15.2 | 14.8 | 15 | 15.3 | 0 | 0 | 0 | 0 | 19.5 |
| Rh | ppm by mass | 503 | 505 | 497 | 503 | 505 | 0 | 0 | 0 | 0 | 670 |
| Acetic acid | % by mass | Balance | Balance | Balance | Balance | Balance | Balance | Balance | Balance | Balance | Balance |
| $PH_2$ | kPa (absolute pressure) | 510 | 550 | 561 | 510 | 550 | 5.3 | 5.4 | 5.1 | 1.1 | 5.3 |
| $PCO_2$ | kPa (absolute pressure) | 72 | 81 | 85 | 72 | 81 | 9.9 | 10 | 2.2 | 1.2 | 2.3 |
| PCO | *Mpa (absolute pressure) | 1.6 | 1.3 | 0.9 | 1.5 | 1.2 | 21 | 21 | 10 | 10 | 0.004 |
| Temperature | °C. | 180 | 180 | 180 | 170 | 170 | 100 | 100 | 100 | 100 | 145 |
| Retention time | min | 30 | | | 30 | | | 30 | 30 | 30 | 5 |
| Formic acid concentration at the completion | ppm by mass | | 88 | | | 102 | | 49 | 48 | 50 | 49 |

*kPa (absolute pressure) in Comparative Examples 3 to 5

| | | Examples | | | | | | | | | | |
|---|---|---|---|---|---|---|---|---|---|---|---|---|
| | | 1 | | 2 | | 3 | | 4 | | 5 | 6 | 7 |
| | | Start | 8 min later | Start | 9 min later | Start | 5 min later | Start | 8 min later | Start | Start | Start |
| Formic acid | ppm by mass | 0 | 37 | 0 | 28 | 0 | 20 | 0 | 17 | 52 | 50 | 51 |
| Mel | % by mass | 10 | 9.8 | 10 | 9.9 | 10.2 | 9.9 | 10 | 9.9 | 39 | 4.9 | 0 |
| MA | % by mass | 3.9 | 2.9 | 3.8 | 3.1 | 3.7 | 3.2 | 4.3 | 3.5 | 5.5 | 5.3 | 0 |
| Water | % by mass | 2.8 | 2.4 | 1.9 | 1.7 | 2.1 | 2.0 | 2.4 | 2.2 | 2.1 | 51.5 | 0.2 |
| LiI | % by mass | 15 | 15.2 | 14.9 | 15.2 | 15.1 | 15.2 | 15 | 15.2 | 0 | 0 | 0 |
| Rh | ppm by mass | 500 | 501 | 500 | 497 | 507 | 501 | 510 | 503 | 0 | 0 | 0 |
| Acetic acid | % by mass | Balance | Balance | Balance | Balance | Balance | Balance | Balance | Balance | Balance | Balance | Balance |
| $PH_2$ | kPa (absolute pressure) | 105 | 540 | 50 | 538 | 20 | 550 | 510 | 550 | 4.9 | 5.2 | 0.9 |
| $PCO_2$ | kPa (absolute pressure) | 69 | 81 | 85 | 79 | 60 | 81 | 72 | 81 | 10.5 | 2.1 | 1.1 |
| PCO | *Mpa (absolute pressure) | 1.6 | 1.3 | 1.6 | 1.2 | 1.6 | 1.2 | 1.5 | 1.2 | 20.2 | 9.9 | 10.5 |
| Temperature | °C. | 180 | 180 | 180 | 180 | 180 | 180 | 188 | 180 | 110 | 110 | 110 |
| Retention Time | min | 30 | | 30 | | 30 | | 30 | | 30 | 30 | 30 |
| Formic acid concentration at the completion | ppm by mass | | 48 | | 35 | | 28 | | 21 | 45 | 43 | 44 |

| | | 8 | 9 | 10 | 11 | 12 | 13 | 14 | 15 | 16 | 17 | 18 |
|---|---|---|---|---|---|---|---|---|---|---|---|---|
| | | Start | Start | Start | Start | Start | Start | Start | Start | Start | Start | Start |
| Formic acid | ppm by mass | 52 | 50 | 51 | 52 | 52 | 52 | 50 | 52 | 52 | 52 | 50 |
| Mel | % by mass | 40 | 5 | 0 | 0 | 0 | 0 | 5 | 40 | 40 | 40 | 1 |
| MA | % by mass | 5 | 5 | 0 | 0 | 0 | 0 | 5 | 5 | 6 | 5 | 1.1 |
| Water | % by mass | 2 | 50 | 0.2 | 0.1 | 0.1 | 0.1 | 5 | 2 | 2 | 2 | 2.3 |
| LiI | % by mass | 0 | 0 | 0 | 0 | 0 | 0 | 0 | 0 | 0 | 0 | 19.6 |
| Rh | ppm by mass | 0 | 0 | 0 | 0 | 0 | 0 | 0 | 0 | 0 | 0 | 670 |
| Acetic acid | % by mass | Balance | Balance | Balance | Balance | Balance | Balance | Balance | Balance | Balance | Balance | Balance |
| $PH_2$ | kPa (absolute pressure) | 4.8 | 5.2 | 0.9 | 1.1 | 1.1 | 1.1 | 5.3 | 0.48 | 0.5 | 0.49 | 1.2 |
| $PCO_2$ | kPa (absolute pressure) | 9.9 | 1.9 | 1.2 | 1 | 1 | 1 | 2.1 | 0.31 | 0.29 | 0.32 | 0.5 |
| PCO | *Mpa (absolute pressure) | 21 | 10.1 | 9.8 | 10 | 10 | 0 | 10.3 | 4.2 | 3.9 | 4.1 | 0.004 |
| Temperature | °C. | 120 | 120 | 120 | 140 | 150 | 150 | 150 | 120 | 120 | 120 | 145 |
| Retention Time | min | 30 | 30 | 30 | 30 | 30 | 30 | 30 | 30 | 5 | 2 | 5 |
| Formic acid concentration at the completion | ppm by mass | 38 | 32 | 36 | 22 | 13 | 15 | 17 | 31 | 39 | 44 | 38 |

*kPa (absolute pressure) in Comperative Examples 3 to 5

[Discussion on Results]

From Comparative Example 1 and Examples 1 to 3, it is evident that at lower $H_2$ and $CO_2$ partial pressures, the amount of formic acid formed is smaller, and formic acid is formed substantially in proportion to the $H_2$ and $CO_2$ partial pressures.

From Comparative Examples 1 and 2 and Example 4, it is evident that at a higher temperature, formic acid formation is suppressed.

From Comparative Example 3 and Examples 5 and 8, it is evident that at a higher temperature, the decomposition of formic acid is promoted even under conditions different from the composition of Comparative Example 1.

From Comparative Example 4 and Examples 6 and 9, it is evident that at a higher temperature, the decomposition of formic acid is promoted even under conditions different from the composition of Comparative Example 1.

From Comparative Example 5 and Examples 7 and 10, it is evident that at a higher temperature, the decomposition of formic acid is promoted even under conditions different from the composition of Comparative Example 1.

From Examples 11 and 12, it is evident that at a higher temperature, the decomposition of formic acid is promoted even under conditions different from the composition of Comparative Example 1.

From Examples 12 and 13, it is evident that even the absence of CO hardly influence a formic acid decomposition rate.

Although Examples 14 and 12 differ somewhat in composition, it is evident that under high temperature conditions, the decomposition of formic acid is similarly promoted.

From Examples 8 and 15, it is evident that the decomposition of formic acid is promoted as the $H_2$ and $CO_2$ partial pressures are reduced.

From Examples 15 to 17, it is evident that at a longer retention time, the decomposition of formic acid is promoted.

From Comparative Example 6 and Example 18, it is evident that the decomposition of formic acid is promoted as the $H_2$ and $CO_2$ partial pressures are reduced.

Specifically, the present invention relates to the following:

Appendix 1: A method for producing acetic acid, comprising at least one step selected from a step that satisfies the following operating conditions (i) and a step that satisfies the following operating conditions (ii) in an acetic acid production process:

(i) operating conditions involving a hydrogen partial pressure of less than 500 kPa (absolute pressure), a carbon dioxide partial pressure of less than 70 kPa (absolute pressure), and an operating temperature of more than 175° C.; and (ii) operating conditions involving a hydrogen partial pressure of not more than 5 kPa (absolute pressure), a carbon dioxide partial pressure of less than 20 kPa (absolute pressure), and an operating temperature of more than 100° C.

Appendix 2: The method for producing acetic acid according to appendix 1, wherein the operating conditions (i) involve a hydrogen partial pressure (absolute pressure) of not more than 400 kPa (preferably not more than 300 kPa, more preferably not more than 200 kPa, further preferably not more than 150 kPa).

Appendix 3: The method for producing acetic acid according to appendix 1 or 2, wherein the operating conditions (i) involve a hydrogen partial pressure (absolute pressure) of more than 1 kPa (or more than 5 kPa).

Appendix 4: The method for producing acetic acid according to any one of appendixes 1 to 3, wherein the operating conditions (i) involve a carbon dioxide partial pressure (absolute pressure) of not more than 60 kPa (preferably not more than 50 kPa, more preferably not more than 40 kPa, further preferably not more than 30 kPa).

Appendix 5: The method for producing acetic acid according to any one of appendixes 1 to 4, wherein the operating conditions (i) involve a carbon dioxide partial pressure (absolute pressure) of not less than 2 kPa (or not less than 20 kPa).

Appendix 6: The method for producing acetic acid according to any one of appendixes 1 to 5, wherein the operating conditions (i) involve an operating temperature of not less than 178° C. (preferably not less than 181° C., more preferably not less than 184° C.).

Appendix 7: The method for producing acetic acid according to any one of appendixes 1 to 6, wherein the operating conditions (i) involve an operating temperature of not more than 250° C. (preferably not more than 230° C., more preferably not more than 200° C.).

Appendix 8: The method for producing acetic acid according to any one of appendixes 1 to 7, wherein the operating conditions (ii) involve a hydrogen partial pressure (absolute pressure) of not more than 4 kPa (preferably not more than 3 kPa, more preferably not more than 2 kPa, further preferably not more than 1 kPa).

Appendix 9: The method for producing acetic acid according to any one of appendixes 1 to 8, wherein the operating conditions (ii) involve a carbon dioxide partial pressure (absolute pressure) of not more than 18 kPa (preferably not more than 16 kPa, more preferably not more than 14 kPa, further preferably not more than 12 kPa).

Appendix 10: The method for producing acetic acid according to any one of appendixes 1 to 9, wherein the operating conditions (ii) involve an operating temperature of not less than 102° C. (preferably not less than 104° C., more preferably not less than 106° C., further preferably not less than 112° C.).

Appendix 11: The method for producing acetic acid according to any one of appendixes 1 to 10, wherein the operating conditions (ii) involve an operating temperature of not more than 250° C. (preferably not more than 200° C., more preferably not more than 175° C.).

Appendix 12: The method for producing acetic acid according to any one of appendixes 1 to 11, wherein the operating conditions (ii) involve a hydrogen partial pressure of not more than 1 kPa (absolute pressure) and a carbon dioxide partial pressure of less than 2 kPa (absolute pressure).

Appendix 13: The method for producing acetic acid according to appendix 12, wherein the operating conditions (ii) involve a hydrogen partial pressure (absolute pressure) of not more than 0.9 kPa (preferably not more than 0.8 kPa).

Appendix 14: The method for producing acetic acid according to appendix 12 or 13, wherein the operating conditions (ii) involve a carbon dioxide partial pressure (absolute pressure) of not more than 1.8 kPa (preferably not more than 1.5 kPa, more preferably not more than 1.0 kPa, further preferably not more than 0.5 kPa).

Appendix 15: The method for producing acetic acid according to any one of appendixes 1 to 14, wherein the method has a reaction step that satisfies the operating conditions (i).

Appendix 16: The method for producing acetic acid according to appendix 15, wherein a reaction mixture liquid in the reaction step has an acetic acid concentration of not less than 30% by mass (e.g., 30 to 90% by mass) and a formic acid concentration of not more than 102 ppm by mass (e.g., 0 to 102 ppm by mass).

Appendix 17: The method for producing acetic acid according to appendix 15 or 16, wherein a reaction mixture liquid in the reaction step has an acetic acid concentration of 50 to 90% by mass (e.g., 60 to 80% by mass), a metal catalyst concentration (in terms of the metal) of 200 to 10000 ppm by mass (e.g., 200 to 5000 ppm by mass, preferably 400 to 2000 ppm by mass), a methyl iodide concentration of 1 to 20% by mass (e.g., 5 to 15% by mass), an ionic iodide concentration of 1 to 25% by mass (e.g., 5 to 20% by mass), a water concentration of 0.1 to 15% by mass (e.g., 0.8 to 10% by mass), a methyl acetate concentration of 0.1 to 30% by mass (e.g., 1 to 10% by mass), and a formic acid concentration of not more than 102 ppm by mass (e.g., not more than 85 ppm by mass).

Appendix 18: The method for producing acetic acid according to any one of appendixes 15 to 17, wherein the reaction mixture in the reaction step has a formic acid concentration of 0 to 102 ppm by mass (preferably 0 to 85 ppm by mass, more preferably 0 to 50 ppm by mass).

Appendix 19: The method for producing acetic acid according to any one of appendixes 1 to 18, wherein the method has an evaporation step or a distillation step that satisfies the operating conditions (ii).

Appendix 20: The method for producing acetic acid according to appendix 19, wherein a charging mixture for an evaporator in the evaporation step has an acetic acid concentration of 50 to 90% by mass (e.g., 60 to 80% by mass), a metal catalyst concentration (in terms of the metal) of 200 to 10000 ppm by mass (e.g., 200 to 5000 ppm by mass, preferably 400 to 2000 ppm by mass), a methyl iodide concentration of 1 to 20% by mass (e.g., 5 to 15% by mass), an ionic iodide concentration of 1 to 25% by mass (e.g., 5 to 20% by mass), a water concentration of 0.1 to 15% by mass (e.g., 0.8 to 10% by mass), a methyl acetate concentration of 0.1 to 30% by mass (e.g., 1 to 10% by mass), a formic acid concentration of not more than 10000 ppm by mass (e.g., 0 to 1000 ppm by mass, preferably 10 to 500 ppm by mass, further preferably 15 to 200 ppm by mass, particularly preferably 20 to 100 ppm by mass).

Appendix 21: The method for producing acetic acid according to appendix 19, wherein a charging mixture for a distillation column in the distillation step has an acetic acid concentration of not less than 30% by mass (e.g., 30 to 99.999% by mass) and a formic acid concentration of not less than 5 ppm by mass (e.g., 5 to 10000 ppm by mass).

Appendix 22: The method for producing acetic acid according to appendix 19, wherein a charging mixture for a distillation column in the distillation step has an acetic acid concentration of 40 to 85% by mass (e.g., 50 to 75% by mass), a methyl iodide concentration of 2 to 50% by mass (e.g., 5 to 30% by mass), a water concentration of 0.2 to 20% by mass (e.g., 1 to 15% by mass), a methyl acetate concentration of 0.2 to 50% by mass (e.g., 2 to 30% by mass), and a formic acid concentration of 5 to 10000 ppm by mass (e.g., 10 to 1000 ppm by mass, preferably 10 to 500 ppm by mass, further preferably 15 to 200 ppm by mass, particularly preferably 20 to 100 ppm by mass).

Appendix 23: The method for producing acetic acid according to appendix 19, wherein a charging mixture for a distillation column in the distillation step has an acetic acid concentration of 80 to 99.9% by mass (e.g., 90 to 99.9% by mass, preferably 93 to 99% by mass), a methyl iodide concentration of 0.01 to 16% by mass (e.g., 0.1 to 8% by mass, preferably 0.2 to 5% by mass), a water concentration of 0.05 to 18% by mass (e.g., 0.1 to 8% by mass, preferably 0.2 to 5% by mass), a methyl acetate concentration of 0.01 to 16% by mass (e.g., 0.1 to 8% by mass, preferably 0.2 to 5% by mass), and a formic acid concentration of 5 to 10000 ppm by mass (e.g., 10 to 1000 ppm by mass, preferably 10 to 500 ppm by mass, further preferably 15 to 200 ppm by mass, particularly preferably 20 to 100 ppm by mass).

Appendix 24: The method for producing acetic acid according to appendix 19, wherein a charging mixture for a distillation column in the distillation step has an acetic acid concentration of 99.1 to 99.999% by mass and a formic acid concentration of 5 to 9000 ppm by mass (e.g., 10 to 1000 ppm by mass, preferably 10 to 500 ppm by mass, further preferably 15 to 200 ppm by mass, particularly preferably 20 to 100 ppm by mass).

Appendix 25: The method for producing acetic acid according to any one of appendixes 1 to 24, wherein the acetic acid production process has a carbonylation reaction step of reacting methanol with carbon monoxide to produce acetic acid, an evaporation step of separating the reaction mixture obtained in the carbonylation reaction step into a vapor stream and a residual liquid stream, and a lower boiling point component removal step of separating the vapor stream by distillation into an overhead stream rich in lower boiling point component and a first acetic acid stream rich in acetic acid, or wherein the acetic acid production process further has at least one of the following steps (a)-(d) in addition to the carbonylation reaction step, the evaporation step, and the lower boiling point component removal step:
(a) a dehydration step of separating the first acetic acid stream by distillation into an overhead stream rich in water and a second acetic acid stream more enriched with acetic acid than the first acetic acid stream,
(b) a higher boiling point component removal step of separating the first acetic acid stream or the second acetic acid stream by distillation into a bottom stream rich in higher boiling point component and a third acetic acid stream more enriched with acetic acid than the acetic acid stream before the distillation,
(c) an adsorptive removal step of treating the first acetic acid stream, the second acetic acid stream, or the third acetic acid stream with an ion exchange resin to obtain a fourth acetic acid stream, and
(d) a product step of distilling the first acetic acid stream, the second acetic acid stream, the third acetic acid stream or the fourth acetic acid stream to obtain a fifth acetic acid stream more enriched with acetic acid than the acetic acid stream before the distillation.

Appendix 26: The method for producing acetic acid according to appendix 25, wherein the carbonylation reaction step satisfies the operating conditions (i).

Appendix 27: The method for producing acetic acid according to appendix 25 or 26, wherein at least one step selected from the evaporation step, the lower boiling point component removal step, the dehydration step, the higher boiling point component removal step, and the product step satisfies the operating conditions (ii).

Appendix 28: The method for producing acetic acid according to any one of appendixes 25 to 27, wherein the evaporation step satisfies the operating conditions (ii).

Appendix 29: The method for producing acetic acid according to appendix 28, wherein the operating conditions (ii) satisfied by the evaporation step involve a hydrogen partial pressure (absolute pressure) of not more than 4 kPa (preferably not more than 3 kPa, more preferably not more than 1 kPa, further preferably not more than 0.8 kPa).

Appendix 30: The method for producing acetic acid according to appendix 28 or 29, wherein the operating conditions (ii) satisfied by the evaporation step involve a carbon dioxide partial pressure (absolute pressure) of not more than 12 kPa (preferably not more than 8 kPa, more preferably not more than 3 kPa, further preferably not more than 1 kPa).

Appendix 31: The method for producing acetic acid according to any one of appendixes 28 to 30, wherein the operating conditions (ii) satisfied by the evaporation step involve an operating temperature of not less than 112° C. (preferably not less than 120° C., more preferably not less than 130° C.; the upper limit is, for example, 260° C., preferably 200° C., more preferably 180° C. (or 170° C. or 160° C.)).

Appendix 32: The method for producing acetic acid according to any one of appendixes 25 to 31, wherein the lower boiling point component removal step satisfies the operating conditions (ii).

Appendix 33: The method for producing acetic acid according to appendix 32, wherein the operating conditions (ii) satisfied by the lower boiling point component removal step involve a hydrogen partial pressure (absolute pressure) of not more than 4 kPa (preferably not more than 3 kPa, more preferably not more than 1 kPa).

Appendix 34: The method for producing acetic acid according to appendix 32 or 33, wherein the operating conditions (ii) satisfied by the lower boiling point component removal step involve a carbon dioxide partial pressure (absolute pressure) of not more than 12 kPa (preferably not more than 8 kPa, more preferably not more than 3 kPa, further preferably not more than 1 kPa).

Appendix 35: The method for producing acetic acid according to any one of appendixes 32 to 34, wherein the operating conditions (ii) satisfied by the lower boiling point component removal step involve an operating temperature of not less than 112° C. (preferably not less than 114° C.; the upper limit is, for example, 165° C., preferably 160° C., more preferably 150° C. (or 140° C. or 130° C.)).

Appendix 36: The method for producing acetic acid according to any one of appendixes 32 to 35, wherein a charging mixture for a distillation column in the lower boiling point component removal step has an acetic acid concentration of not less than 30% by mass (e.g., 30 to 99.999% by mass) and a formic acid concentration of not less than 5 ppm by mass (e.g., 5 to 10000 ppm by mass).

Appendix 37: The method for producing acetic acid according to any one of appendixes 32 to 35, wherein a charging mixture for a distillation column in the lower boiling point component removal step has an acetic acid concentration of 40 to 85% by mass (e.g., 50 to 85% by mass, preferably 50 to 75% by mass, more preferably 55 to 75% by mass), a methyl iodide concentration of 2 to 50% by mass (e.g., 5 to 30% by mass), a water concentration of 0.2 to 20% by mass (e.g., 1 to 15% by mass), a methyl acetate concentration of 0.2 to 50% by mass (e.g., 2 to 30% by mass), and a formic acid concentration of 5 to 10000 ppm by mass (e.g., 10 to 1000 ppm by mass, more preferably 10 to 500 ppm by mass, particularly, 15 to 200 ppm by mass, in particular, 20 to 100 ppm by mass).

Appendix 38: The method for producing acetic acid according to any one of appendixes 25 to 37, wherein the dehydration step satisfies the operating conditions (ii).

Appendix 39: The method for producing acetic acid according to appendix 38, wherein the operating conditions (ii) satisfied by the dehydration step involve a hydrogen partial pressure (absolute pressure) of not more than 2 kPa (preferably not more than 1 kPa, more preferably not more than 0.5 kPa).

Appendix 40: The method for producing acetic acid according to appendix 38 or 39, wherein the operating conditions (ii) satisfied by the dehydration step involve a carbon dioxide partial pressure (absolute pressure) of not more than 5 kPa (preferably not more than 2 kPa, more preferably not more than 1 kPa, further preferably not more than 0.5 kPa).

Appendix 41: The method for producing acetic acid according to any one of appendixes 38 to 40, wherein the operating conditions (ii) satisfied by the dehydration step involve an operating temperature of not less than 120° C. (preferably not less than 130° C.; the upper limit is, for example, 170° C., preferably 165° C., more preferably 160° C., further preferably 155° C.).

Appendix 42: The method for producing acetic acid according to any one of appendixes 38 to 41, wherein a charging mixture for a distillation column in the dehydration step has an acetic acid concentration of not less than 30% by mass (e.g., 30 to 99.999% by mass) and a formic acid concentration of not less than 5 ppm by mass (e.g., 5 to 10000 ppm by mass).

Appendix 43: The method for producing acetic acid according to any one of appendixes 38 to 41, wherein a charging mixture for a distillation column in the dehydration step has an acetic acid concentration of 80 to 99.9% by mass (e.g., 90 to 99.9% by mass, particularly, 93 to 99% by mass), a methyl iodide concentration of 0.01 to 16% by mass (e.g., 0.1 to 8% by mass, particularly, 0.2 to 5% by mass), a water concentration of 0.05 to 18% by mass (e.g., 0.1 to 8% by mass, particularly, 0.2 to 5% by mass), a methyl acetate concentration of 0.01 to 16% by mass (e.g., 0.1 to 8% by mass, particularly, 0.2 to 5% by mass), and a formic acid concentration of 5 to 10000 ppm by mass (e.g., 10 to 1000 ppm by mass, more preferably 10 to 500 ppm by mass, particularly, 15 to 200 ppm by mass, in particular, 20 to 100 ppm by mass).

Appendix 44: The method for producing acetic acid according to any one of appendixes 25 to 43, wherein the higher boiling point component removal step satisfies the operating conditions (ii).

Appendix 45: The method for producing acetic acid according to appendix 44, wherein the operating conditions (ii) satisfied by the higher boiling point component removal step involve a hydrogen partial pressure (absolute pressure) of not more than 2 kPa (preferably not more than 1 kPa, more preferably not more than 0.5 kPa).

Appendix 46: The method for producing acetic acid according to appendix 44 or 45, wherein the operating conditions (ii) satisfied by the higher boiling point component removal step involve a carbon dioxide partial pressure (absolute pressure) of not more than 5 kPa (preferably not more than 2 kPa, more preferably not more than 1 kPa, further preferably not more than 0.5 kPa).

Appendix 47: The method for producing acetic acid according to any one of appendixes 44 to 46, wherein the operating conditions (ii) satisfied by the higher boiling point component removal step involve an operating temperature of not less than 120° C. (preferably not less than 130° C.; the upper limit is, for example, 165° C., preferably 160° C., further preferably 155° C.).

Appendix 48: The method for producing acetic acid according to any one of appendixes 44 to 47, wherein a charging mixture for a distillation column in the higher boiling point component removal step has an acetic acid concentration of 99.1 to 99.99% by mass and a formic acid concentration of 5 to 9000 ppm by mass (e.g., 10 to 1000 ppm by mass, more preferably 10 to 500 ppm by mass, particularly, 15 to 200 ppm by mass, in particular, 20 to 100 ppm by mass).

Appendix 49: The method for producing acetic acid according to any one of appendixes 25 to 48, wherein the product step satisfies the operating conditions (ii).

Appendix 50: The method for producing acetic acid according to appendix 49, wherein the operating conditions (ii) satisfied by the product step involve a hydrogen partial pressure (absolute pressure) of not more than 2 kPa (preferably not more than 1 kPa, more preferably not more than 0.5 kPa).

Appendix 51: The method for producing acetic acid according to appendix 49 or 50, wherein the operating conditions (ii) satisfied by the product step involve a carbon dioxide partial pressure (absolute pressure) of not more than 5 kPa (preferably not more than 2 kPa, more preferably not more than 1 kPa, further preferably not more than 0.5 kPa).

Appendix 52: The method for producing acetic acid according to any one of appendixes 49 to 51, wherein the operating conditions (ii) satisfied by the product step involve an operating temperature of not less than 120° C. (preferably not less than 130° C.; the upper limit is, for example, 165° C., preferably 160° C., more preferably 155° C.).

Appendix 53: The method for producing acetic acid according to any one of appendixes 49 to 52, wherein a charging mixture for a product column in the product step has an acetic acid concentration of 99.8 to 99.999% by mass and a formic acid concentration of 5 to 2000 ppm by mass (e.g., 5 to 1000 ppm by mass, particularly, 5 to 100 ppm by mass).

Appendix 54: The method for producing acetic acid according to any one of appendixes 1 to 53, wherein a retention time in the step that satisfies the operating conditions (i) or the step that satisfies the operating conditions (ii) is not less than 1 minute (e.g., not less than 5 minutes, particularly, not less than 10 minutes).

Appendix 55: The method for producing acetic acid according to appendix 54, wherein the retention time in the step that satisfies the operating conditions (i) or the step that satisfies the operating conditions (ii) is not more than 2 hours (preferably not more than 1 hour).

Appendix 56: The method for producing acetic acid according to any one of appendixes 1 to 55, wherein a process solution having a formic acid concentration of not less than 10 ppm by mass (e.g., 10 to 10000 ppm by mass, preferably 15 to 1000 ppm by mass, further preferably 20 to 200 ppm by mass) is recycled to a step that satisfies (iii) operating conditions involving a hydrogen partial pressure of less than 500 kPa (absolute pressure), a carbon dioxide partial pressure of less than 70 kPa (absolute pressure), and an operating temperature of more than 100° C.

Appendix 57: The method for producing acetic acid according to any one of appendixes 1 to 56, wherein the acetic acid production process has at least one distillation step, and a column top fraction of a distillation column in the at least one distillation step is recycled to the step that satisfies the operating conditions (i) and/or the step that satisfies the operating conditions (ii).

Appendix 58: The method for producing acetic acid according to appendix 57, wherein the step to which the column top fraction of a distillation column is recycled is the reaction step and/or the evaporation step or a distillation step positioned upstream from the distillation step associated with the distillation column.

Appendix 59: The method for producing acetic acid according to appendix 57 or 58, wherein the step that satisfies the operating conditions (iii) is at least one step selected from the reaction step, the evaporation step, the lower boiling point component removal step, and the dehydration step.

INDUSTRIAL APPLICABILITY

The method for producing acetic acid of the present invention can be used as industrial method for producing acetic acid by carbonylation process of a methanol method (acetic acid process of a methanol method).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:
1. A method for producing acetic acid, comprising at least one step selected from
  a carbonylation reaction step that satisfies the following operating conditions (i) and
  an evaporation step or a distillation step that satisfies the following operating conditions (ii) in an acetic acid production process:
  (i) operating conditions involving a hydrogen partial pressure of more than 1 kPa and less than 500 kPa (absolute pressure), a carbon dioxide partial pressure of not less than 2 kPa and less than 70 kPa (absolute pressure), and an operating temperature of more than 175° C. and not more than 250° C.; and
  (ii) operating conditions involving a hydrogen partial pressure of not less than 0 kPa and not more than 5 kPa (absolute pressure), a carbon dioxide partial pressure of not less than 0 kPa and less than 20 kPa (absolute pressure), and an operating temperature of more than 100° C. and not more than 250° C., wherein
  the acetic acid production process has at least one distillation step,
  a column top fraction of a distillation column in the at least one distillation step is recycled to the carbonylation reaction step that satisfies the operating conditions (i), the evaporation step that satisfies the oper- ating conditions (ii), and/or the distillation step that satisfies the operating conditions (ii) positioned upstream from the distillation step associated with the distillation column, and the carbonylation reaction step that satisfies the operating conditions (i) or the evaporation step or the distillation step that satisfies the operating conditions (ii) decomposes formic acid in the column top fraction.

2. The method for producing acetic acid according to claim 1, wherein the operating conditions (ii) involve a hydrogen partial pressure of not more than 1 kPa (absolute pressure) and a carbon dioxide partial pressure of less than 2 kPa (absolute pressure).

3. The method for producing acetic acid according to claim 1, wherein the method has the carbonylation reaction step that satisfies the operating conditions (i).

4. The method for producing acetic acid according to claim 3, wherein a reaction mixture liquid in the carbonylation reaction step has an acetic acid concentration of not less than 30% by mass and a formic acid concentration of not more than 102 ppm by mass.

5. The method for producing acetic acid according to claim 3, wherein a reaction mixture liquid in the reaction step has an acetic acid concentration of 50 to 90% by mass, a metal catalyst concentration (in terms of the metal) of 200 to 10000 ppm by mass, a methyl iodide concentration of 1 to 20% by mass, an ionic iodide concentration of 1 to 25% by mass, a water concentration of 0.1 to 15% by mass, a methyl acetate concentration of 0.1 to 30% by mass, and a formic acid concentration of not more than 102 ppm by mass.

6. The method for producing acetic acid according to claim 1, wherein the method has the evaporation step or the distillation step that satisfies the operating conditions (ii).

7. The method for producing acetic acid according to claim 6, wherein a charging mixture for an evaporator in the evaporation step has an acetic acid concentration of 50 to 90% by mass, a metal catalyst concentration (in terms of the metal) of 200 to 10000 ppm by mass, a methyl iodide concentration of 1 to 20% by mass, an ionic iodide concentration of 1 to 25% by mass, a water concentration of 0.1 to 15% by mass, a methyl acetate concentration of 0.1 to 30% by mass, and a formic acid concentration of not more than 10000 ppm by mass.

8. The method for producing acetic acid according to claim 6, wherein a charging mixture for a distillation column in the distillation step that satisfies the operating conditions (ii) has an acetic acid concentration of not less than 30% by mass and a formic acid concentration of not less than 5 ppm by mass.

9. The method for producing acetic acid according to claim 6, wherein a charging mixture for a distillation column in the distillation step that satisfies the operating conditions (ii) has an acetic acid concentration of 40 to 85% by mass, a methyl iodide concentration of 2 to 50% by mass, a water concentration of 0.2 to 20% by mass, a methyl acetate concentration of 0.2 to 50% by mass, and a formic acid concentration of 5 to 10000 ppm by mass.

10. The method for producing acetic acid according to claim 6, wherein a charging mixture for a distillation column in the distillation step that satisfies the operating conditions (ii) has an acetic acid concentration of 80 to 99.9% by mass, a methyl iodide concentration of 0.01 to 16% by mass, a water concentration of 0.05 to 18% by mass, a methyl acetate concentration of 0.01 to 16% by mass, and a formic acid concentration of 5 to 10000 ppm by mass.

11. The method for producing acetic acid according to claim 6, wherein a charging mixture for a distillation column in the distillation step that satisfies the operating conditions (ii) has an acetic acid concentration of 99.1 to 99.999% by mass and a formic acid concentration of 5 to 9000 ppm by mass.

12. The method for producing acetic acid according to claim 1, wherein the acetic acid production process has the carbonylation reaction step of reacting methanol with carbon monoxide to produce acetic acid, the evaporation step of separating the reaction mixture obtained in the carbonylation reaction step into a vapor stream and a residual liquid stream, and a lower boiling point component removal step of separating the vapor stream by distillation into an overhead stream rich in lower boiling point component and a first acetic acid stream rich in acetic acid, or wherein the acetic acid production process further has at least one of the following steps (a)-(d) in addition to the carbonylation reaction step, the evaporation step, and the lower boiling point component removal step:

(a) a dehydration step of separating the first acetic acid stream by distillation into an overhead stream rich in water and a second acetic acid stream more enriched with acetic acid than the first acetic acid stream, (b) a higher boiling point component removal step of separating the first acetic acid stream or the second acetic acid stream by distillation into a bottom stream rich in higher boiling point component and a third acetic acid stream more enriched with acetic acid than the acetic acid stream before the distillation, (c) an adsorptive removal step of treating the first acetic acid stream, the second acetic acid stream, or the third acetic acid stream with an ion exchange resin to obtain a fourth acetic acid stream, and (d) a product step of distilling the first acetic acid stream, the second acetic acid stream, the third acetic acid stream or the fourth acetic acid stream to obtain a fifth acetic acid stream more enriched with acetic acid than the acetic acid stream before the distillation.

13. The method for producing acetic acid according to claim 12, wherein at least one step selected from the evaporation step, the lower boiling point component removal step, the dehydration step, the higher boiling point component removal step, and the product step satisfies the operating conditions (ii).

14. The method for producing acetic acid according to claim 1, wherein a retention time in the step that satisfies the operating conditions (i) or the step that satisfies the operating conditions (ii) is not less than 1 minute.

15. The method for producing acetic acid according to claim 1, wherein a process solution having a formic acid concentration of not less than 10 ppm by mass is recycled to a step that satisfies operating conditions involving a hydrogen partial pressure of less than 500 kPa (absolute pressure), a carbon dioxide partial pressure of less than 70 kPa (absolute pressure), and an operating temperature of more than 100° C.

16. The method for producing acetic acid according to claim 1, wherein the column top fraction to be recycled is a column top fraction of a distillation column that a charging mixture for the distillation column has an acetic acid concentration of 80 to 99.999% by mass.

17. The method for producing acetic acid according to claim 1, wherein the operating conditions (i) involves a hydrogen partial pressure of not less than 1 and less than 500 kPa (absolute pressure), and the operating conditions (ii) involves a carbon dioxide partial pressure of less than 12 kPa (absolute pressure) and an operating temperature of 106° C. to 250° C.

18. The method for producing acetic acid according to claim 1, wherein a retention time in the step that satisfies the operating conditions (i) or the step that satisfies the operating conditions (ii) is not less than 1 minute and not more than 2 hours.

19. The method for producing acetic acid according to claim 1, wherein the method has a distillation step that satisfies the operating conditions (ii), and a charging mixture for a distillation column in the distillation step that satisfies the operating condition (ii) has a formic acid concentration of 5 to 1000 ppm by mass.

* * * * *